US012734502B2

(12) United States Patent
Kitabata et al.

(10) Patent No.: US 12,734,502 B2
(45) Date of Patent: Sep. 15, 2026

(54) POLY(METH)ACRYLIC ACID (SALT)-BASED WATER-ABSORBING RESIN, AND ABSORBENT BODY

(71) Applicant: NIPPON SHOKUBAI CO., LTD., Osaka (JP)

(72) Inventors: Sachie Kitabata, Hyogo (JP); Satoshi Matsumoto, Hyogo (JP); Kanako Tsuru, Hyogo (JP); Kunihiko Ishizaki, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 505 days.

(21) Appl. No.: 18/289,690

(22) PCT Filed: Apr. 25, 2022

(86) PCT No.: PCT/JP2022/018668
§ 371 (c)(1),
(2) Date: Nov. 6, 2023

(87) PCT Pub. No.: WO2022/239628
PCT Pub. Date: Nov. 17, 2022

(65) Prior Publication Data

US 2024/0253013 A1 Aug. 1, 2024

(30) Foreign Application Priority Data

May 12, 2021 (JP) ................................ 2021-081233
Dec. 21, 2021 (JP) ................................ 2021-207382

(51) Int. Cl.
*B01J 20/26* (2006.01)
*A61L 15/24* (2006.01)
(Continued)

(52) U.S. Cl.
CPC ............. *B01J 20/261* (2013.01); *A61L 15/24* (2013.01); *B01J 20/28004* (2013.01);
(Continued)

(58) Field of Classification Search
None
See application file for complete search history.

(56) References Cited

U.S. PATENT DOCUMENTS

2006/0168841 A1 8/2006 Kouno et al.
2009/0275470 A1* 11/2009 Nagasawa ............ B01J 20/0244 502/402

(Continued)

FOREIGN PATENT DOCUMENTS

CN 101627086 A 1/2010
CN 103459473 A 12/2013

(Continued)

OTHER PUBLICATIONS

Office Action from Chinese Application No. 202280033907.0 dated Jul. 9, 2025.

(Continued)

*Primary Examiner* — John J Figueroa
(74) *Attorney, Agent, or Firm* — Harness Dickey & Pierce P.L.C.

(57) ABSTRACT

An object lies in providing a novel water-absorbing resin and a novel absorbent body both of which enable provision of an absorbent article that prevents swelling of a water-absorbing portion when used in a thin absorbent article. The object is achieved by providing a water-absorbing resin that is a particulate poly(meth)acrylic acid (salt)-based water-absorbing resin and has a swollen gel compressibility rate of 3% or more expressed by Formula 1: Swollen gel compressibility rate [%]=(D1−D2)/D1×100 (Formula 1), where D1 represents a thickness of a swollen gel before compression,
(Continued)

and D2 represents a thickness of a swollen gel after compression.

9 Claims, 2 Drawing Sheets

(51) Int. Cl.
*B01J 20/28* (2006.01)
*B01J 20/30* (2006.01)
*C08F 20/06* (2006.01)

(52) U.S. Cl.
CPC ..... *B01J 20/28019* (2013.01); *B01J 20/2803* (2013.01); *B01J 20/28047* (2013.01); *B01J 20/3007* (2013.01); *B01J 20/3085* (2013.01); *C08F 20/06* (2013.01)

(56) References Cited

U.S. PATENT DOCUMENTS

2009/0312183 A1* 12/2009 Fujimaru .............. C08F 120/06 502/402
2010/0249320 A1* 9/2010 Matsumoto ............... F26B 3/08 524/832
2011/0015351 A1* 1/2011 Nogi ......................... B65B 1/22 525/385
2012/0071848 A1* 3/2012 Zhang ..................... A61L 15/60 428/411.1
2013/0175473 A1* 7/2013 Wada ................... B01J 20/3085 252/194
2015/0011388 A1 1/2015 Matsumoto et al.
2015/0216740 A1 8/2015 Watanabe et al.
2015/0218341 A1* 8/2015 Nakashima ........... A61L 26/008 524/349
2017/0050170 A1 2/2017 Braun et al.
2017/0203279 A1 7/2017 Murakami et al.
2018/0161756 A1 6/2018 Omori et al.
2018/0298132 A1* 10/2018 Yorino .................... A61L 15/00
2021/0022932 A1 1/2021 Ito et al.
2021/0023530 A1 1/2021 Ito et al.
2021/0038439 A1* 2/2021 Torii ................. A61F 13/15617
2021/0298965 A1* 9/2021 Noda ..................... B01J 20/267
2021/0387163 A1* 12/2021 Wada ...................... A61F 13/53

FOREIGN PATENT DOCUMENTS

CN 104974358 A 10/2015
CN 107428949 A 12/2017
EP 3318324 A1 5/2018
EP 4299651 A1 1/2024
JP 09003123 1/1997
JP 3107909 B2 11/2000
JP 4880144 B2 2/2012
JP 2012031292 A 2/2012
JP 2016027846 A 2/2016
JP 7058787 B1 4/2022
KR 101887706 B1 8/2018
WO 2011040530 A1 4/2011
WO 2014038324 A1 3/2014
WO 2019098244 A1 5/2019
WO 2019189445 A1 10/2019
WO 2019189485 A1 10/2019

OTHER PUBLICATIONS

Office Action from Chinese Application No. 202280033907.0 dated Dec. 1, 2025.
Liao Zhengfu et al. (2014). Synthesis of Water-Soluble Solid Polyacrylic Acid by Inverse Suspension Polymerization, China Elastomerics, 24(5): 5-7.
Benda, D. et al. (1997). Inverse Suspension Polymerization of the Hydrophilic Acrylic Monomers in the Static Continuous Phase. Journal of Dispersion Science and Technology, 18: 115-121.
Search Report from European Patent Application No. 22807331.8 dated Apr. 7, 2025.
International Search Report for PCT/JP2022/018668 dated Jun. 14, 2022.
Written Opinion and Interntational Preliminary Report on Patentability for PCT/JP2022/018668 dated Nov. 14, 2023.

* cited by examiner

POLY(METH)ACRYLIC ACID (SALT)-BASED WATER-ABSORBING RESIN, AND ABSORBENT BODY

PRIORITY STATEMENT

This application is a national stage application under 35 U.S.C. § 371 of PCT International Application No. PCT/JP2022/018668, which has an international filing date of 25 Apr. 2022 and claims priority under 35 U.S.C. § 119 to Japan Patent Application No. 2021-081233 filed on 12 May 2021 and to Japan Patent Application No. 2021-207382 filed on 21 Dec. 2021. The contents of each application recited above are incorporated herein by reference in their entirety.

TECHNICAL FIELD

The present invention relates to a water-absorbing resin and an absorbent body. More specifically, the present invention relates to a poly(meth)acrylic acid (salt)-based water-absorbing resin and an absorbent body.

BACKGROUND ART

In recent years, in hygienic materials such as a disposable diaper, a sanitary napkin, and an incontinence pad, a water-absorbing resin as a constituent material of the hygienic materials is widely utilized as a water-absorbing agent. As such a water-absorbing resin, for example, a hydrolyzate of a starch-acrylonitrile graft copolymer, a neutralized product of a starch-acrylic acid graft polymer, a saponified product of a vinyl acetate-acrylic ester copolymer, a crosslinked product of a partially neutralized (meth)acrylic acid polymer, and the like are known. From the viewpoint of water absorption performance, a poly(meth)acrylic acid (salt)-based water-absorbing resin formed by using a (meth)acrylic acid and/or a salt thereof as a main component of a monomer(s) is industrially most often produced as a water-absorbing resin.

A water-absorbing resin having excellent gel elasticity to prevent gel blocking is known. For example, Patent Literatures 1 to 5 disclose water-absorbing resins that are excellent in elasticity after absorbing water when used as a constituent material of an absorbent body. The water-absorbing resins described in Patent Literatures 1 to 5 can maintain sufficiently high elasticity even in a case where the proportion of fibrous materials in an absorbent core in an absorbent body is low (high-concentration core). Therefore, the techniques described in Patent Literatures 1 to 5 enable thickness reduction without impairing the absorption performance.

CITATION LIST

Patent Literature

[Patent Literature 1]
International Publication No. WO 2019/189485
[Patent Literature 2]
Japanese Patent No. 4880144
[Patent Literature 3]
Japanese Patent No. 3107909
[Patent Literature 4]
Japanese Patent Application Publication Tokukaihei No. 9-3123
[Patent Literature 5]
International Publication No. WO 2019/189445

SUMMARY OF INVENTION

Technical Problem

The water-absorbing resins having excellent elasticity described in the conventional techniques cause a continuation of a state in which the core is swollen because of the water-absorbing resin swollen due to liquid absorption (water absorption) while the absorbent article is worn. This makes the user feel a discomfort.

An embodiment of the present invention has been attained in view of the above problem, and an object thereof is to provide a novel water-absorbing resin and a novel absorbent body both of which enable provision of an absorbent article that prevents swelling of a water-absorbing portion when used in a thin absorbent article.

Solution to Problem

The inventors of the present invention have found, through their own study, that a poly(meth)acrylic acid (salt)-based water-absorbing resin having a high swollen gel compressibility rate is suitable for the provision of an absorbent article that prevents swelling of a water-absorbing portion when used in a thin absorbent article, and have completed the present invention.

That is, a water-absorbing resin in accordance with an embodiment of the present invention is a poly(meth)acrylic acid (salt)-based water-absorbing resin and has a swollen gel compressibility rate of 3% or more expressed by the following (Formula 1):

$$\text{Swollen gel compressibility rate [\%]} = (D1 - D2)/D1 \times 100, \quad \text{(Formula 1)}$$

where D1 is a thickness [mm] of a swollen gel layer formed by the water-absorbing resin when a measurement device which is equipped with a piston having a diameter of 59 mm and a cell having a bottom portion in a mesh form and having an inner diameter of 60 mm and in which 1.0 g of the water-absorbing resin is spread on the bottom portion has been placed in a petri dish containing a 0.9 mass % aqueous sodium chloride solution to allow the water-absorbing resin to absorb the 0.9 mass % aqueous sodium chloride solution for 5 minutes, and D2 is a thickness [mm] of the swollen gel layer formed by the water-absorbing resin after an operation of setting the measurement device on a sieve having a mesh size of 4750 μm, placing a weight on the piston so that a load of 0.7 psi is applied to the swollen gel layer, allowing the cell to stand still for 10 seconds, and then removing the weight has been repeated ten times.

Advantageous Effects of Invention

An embodiment of the present invention brings about the effect of making it possible to provide a water-absorbing resin and an absorbent body both of which enable provision of an absorbent article that prevents swelling of a water-absorbing portion when used in a thin absorbent article.

DESCRIPTION OF EMBODIMENTS

Figure 1:
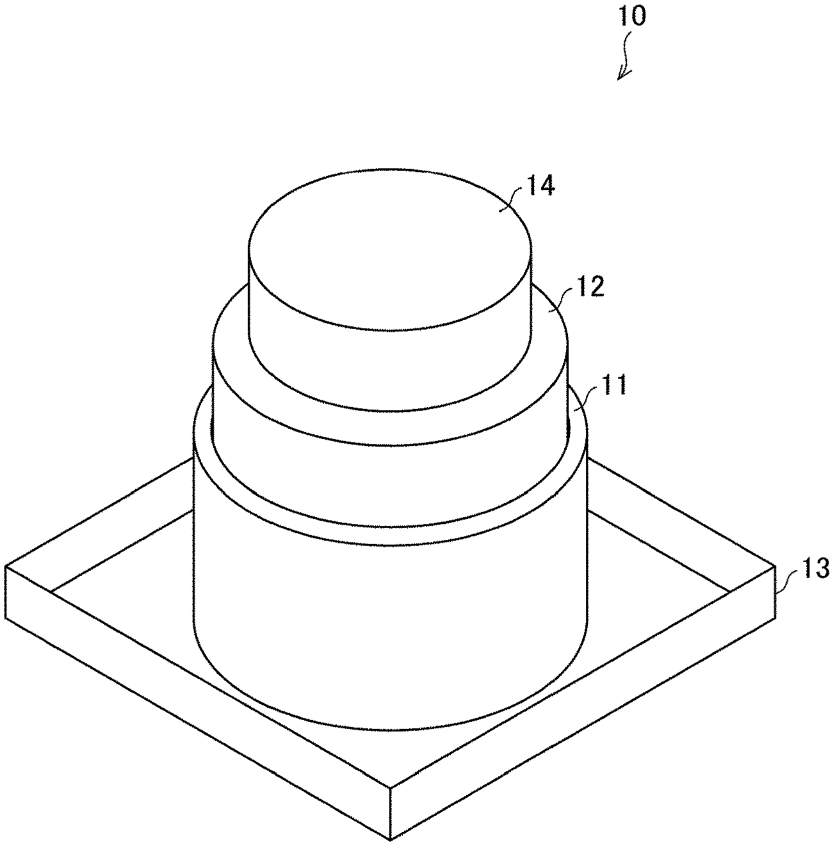
FIG. 1 is a perspective view illustrating an external configuration of a swollen gel compressibility rate measurement device when viewed from one direction.

The following description will discuss the best mode of the present invention. Any term used in the present specification should be understood as ordinarily used in this technical field unless particularly mentioned otherwise. Therefore, unless defined otherwise, all of the technical terms and scientific terms used in the present specification mean as generally understood by a person skilled in the technical field to which the present invention belongs. If there is any conflict in meaning, the present specification (including the definitions) take priority. The present invention is not limited to the embodiments described below and can be altered in various ways within the scope of the claims.

<1> Definitions of Terms

<1-1> Water-Absorbing Resin

The term "water-absorbing resin" as used in an embodiment of the present invention refers to a water-swellable and water-insoluble polymer gelling agent that satisfies the following physical properties. Specifically, the term "water-absorbing resin" refers to a polymer gelling agent that satisfies the following physical properties: CRC (centrifuge retention capacity) defined in ERT 441.2-02 as "water-swelling property" is 5 g/g or more, and Ext (extractable) defined in ERT 470.2-02 as "water-insolubility" is 50 weight % or less.

The water-absorbing resin can be designed as appropriate according to its purpose of use, and is not limited to a particular design. The water-absorbing resin is preferably a hydrophilic crosslinked polymer that has been obtained by crosslinking and polymerizing unsaturated monomers each of which has a carboxyl group. In addition, the water-absorbing resin is not limited to a form in which the water-absorbing resin is wholly (100 mass %) a polymer, and can be in a form of a water-absorbing resin composition containing an additive and the like within a range in which the above-described physical properties (CRC and Ext) are satisfied.

The water-absorbing resin in an embodiment of the present invention may refer to not only an end product but also an intermediate produced during a process of producing the water-absorbing resin (e.g. a crosslinked hydrogel polymer after polymerization (hydrogel polymer), a dried polymer after drying, a water-absorbing resin powder before surface crosslinking, and the like). All these water-absorbing resins, including the water-absorbing resin composition described above, will be collectively referred to as "water-absorbing resin".

Examples of forms of the water-absorbing resin in an embodiment of the present invention encompass a sheet form, a fiber form, a film form, a particulate form, and a gel form. The form of the water-absorbing resin in an embodiment of the present invention is preferably a particulate form. The water-absorbing resin in an embodiment of the present invention is more preferably a particulate poly(meth) acrylic acid (salt)-based water-absorbing resin.

<1-2>"EDANA" and "ERT"

The term "EDANA" is an acronym for the European Disposables and Nonwovens Associations. The term "ERT" is an acronym for EDANA Recommended Test Methods, which are European standard (de facto international standard) measuring methods for water-absorbing resin. For the present invention, physical properties of a water-absorbing resin are measured in conformity with the ERT master copy (2002 revised version; known literature) unless otherwise specified.

<1-3> Others

In the present specification, any range of "X to Y" means "X or more and Y or less".

In the present specification, "ppm" means "mass ppm" unless otherwise specified.

In the present specification, the term " . . . acid (salt)" means " . . . acid and/or a salt thereof". The term "(meth) acrylic" means "acrylic and/or methacrylic". The term "poly (meth)acrylic acid (salt)-based water-absorbing resin" means a water-absorbing resin that contains, as a main component, a repeating unit derived from (meth)acrylic acid (salt), and specifically refers to a water-absorbing resin containing (meth)acrylic acid (salt) that accounts for preferably 50 mol % to 100 mol %, more preferably 70 mol % to 100 mol %, even more preferably 90 mol % to 100 mol %, and particularly preferably substantially 100 mol % of all monomers to be used for polymerization (excluding a crosslinking agent).

In the present specification, the unit of volume "liter" may be denoted as "l" or "L".

In the present specification, the terms "weight" and "mass" are used synonymously, the terms "weight %" and "mass %" are used synonymously, and the terms "parts by weight" and "parts by mass" are used synonymously.

<2> Water-Absorbing Resin

"Shape of Water-Absorbing Resin"

In an embodiment of the present invention, a water-absorbing resin is preferably in the form of particles. Specifically, the particles preferably have a non-uniformly pulverized shape, a spherical shape, a football shape, and an aggregate shape, or the like. Above all, a water-absorbing resin in the form of particles having a spherical shape, an aggregate shape in particular, obtains a high gel compressibility rate. Thus, the water-absorbing resin is more preferably an aggregate-like particle of spherical particles (for example, spherical particles including a poly(meth)acrylic acid (salt)-based water-absorbing resin). Note that the spherical particles of the water-absorbing resin can also be described as primary particles, and the aggregate-like particle of the water-absorbing resin can also be described as an aggregate-like secondary particle formed by aggregation of spherical primary particles. Note here that the "spherical shape" encompasses not only a true spherical shape but also a substantially spherical shape of an aspect ratio of 1.0 to 1.2.

<2-2> CRC

The term "CRC" is an acronym for centrifuge retention capacity and means a water absorption capacity without pressure of a water-absorbing resin.

The CRC of the water-absorbing resin in accordance with an embodiment of the present invention is preferably 30 g/g or more, more preferably 32 g/g or more, and even more preferably 34 g/g or more. The upper limit of the CRC is not particularly limited, and the higher the CRC of a water-absorbing resin is, the more preferable it is. From the viewpoint of a balance of a water-absorbing resin between other physical properties and CRC, the upper limit of the CRC is preferably 50 g/g or less, more preferably 48 g/g or less, and even more preferably 46 g/g or less.

A water-absorbing resin having a CRC of 30 g/g or more achieves a sufficient absorption amount and thus can be suitably used as an absorbent body for an absorbent article such as a disposable diaper. Further, a water-absorbing resin having a CRC of 50 g/g or less prevents or reduces a decrease in the speed at which a body fluid or the like such as urine and/or blood is absorbed by the water-absorbing resin and is thus suitable for use in, for example, a disposable diaper having a high water absorption speed. Note that the value of the CRC can be controlled by changing the type and/or amount of, for example, an internal crosslinking agent and/or a surface-crosslinking agent during production of a water-absorbing resin. With regard to a method for measuring the CRC, an example of the method will be detailed in Examples.

<2-3> Ext

The term "Ext" is an abbreviation for "Extractables" (water-soluble component) and means an amount of water-soluble component extracted from a water-absorbing resin. The water-soluble component is measured in conformity with an EDANA method (ERT 470.2-02).

The Ext of the water-absorbing resin in accordance with an embodiment of the present invention is preferably 30 mass % or less, more preferably 20 mass % or less, and even more preferably 10 mass % or less. The lower limit of the Ext is 0 mass %. From the viewpoint of a balance of a water-absorbing resin between other physical properties and Ext, the lower limit of the Ext is preferably 2 mass % or more and more preferably 4 mass % or more.

A water-absorbing resin having an Ext of 30 mass % or less prevents or reduces a decrease in the speed at which a body fluid or the like such as urine and/or blood is absorbed by the water-absorbing resin and is thus suitable for use in, for example, a disposable diaper having a high water absorption speed. Note that the value of the Ext can be controlled by changing the type and/or amount of, for example, a polymerization initiator, an internal crosslinking agent, and/or a surface-crosslinking agent during production of a water-absorbing resin. Further, the value of the Ext can also be controlled by using a chain transfer agent in the polymerization step during production of a water-absorbing resin.

<2-4> AAP

The term "AAP" is an acronym for "absorption against pressure", and means a water absorption capacity under pressure of a water-absorbing resin. In the present invention, the AAP is measured in conformity with an EDANA method (ERT 442.2-02) except that a load condition is changed to 4.83 kPa (0.7 psi). Specifically, the AAP (absorption capacity under pressure) (unit: g/g) is measured after 0.9 g of water-absorbing resin has been allowed to swell for 1 hour under a load of 4.83 kPa with use of a 0.9 mass % (mass/mass %) aqueous sodium chloride solution.

The AAP of the water-absorbing resin in accordance with an embodiment of the present invention is preferably 18 g/g or more, more preferably 20 g/g or more, and even more preferably 23 g/g or more, from the viewpoint of water absorption property when used in hygienic materials. Further, the upper limit of the AAP of the water-absorbing resin is not particularly limited, and is preferably 40 g/g or less.

<2-5> Moisture Content

The "moisture content" is measured in conformity with an EDANA method (ERT 430.2-02), except that the amount of a sample is changed to 1.0 g, and a drying temperature is changed to 180° C. With regard to a method for measuring the moisture content, an example of the method will be detailed in Examples.

The moisture content of the water-absorbing resin in accordance with an embodiment of the present invention is not particularly limited, and is preferably 1 mass % to 20 mass %, more preferably 1 mass % to 15 mass %, even more preferably 2 mass % to 13 mass %, still more preferably 5 mass % to 13 mass %, further more preferably 8 mass % to 13 mass %, and particularly preferably 10 mass % to 13 mass %. A water-absorbing resin having a moisture content of 1 mass % to 20 mass % prevents or reduces a decrease in the speed at which a body fluid or the like such as urine and/or blood is absorbed by the water-absorbing resin and is thus suitable for use in, for example, a disposable diaper having a high water absorption speed.

<2-6> Mass Average Particle Diameter (D50)

The "mass average particle diameter (D50)" is measured in conformity with "(3) Mass-Average Particle Diameter (D50) and Logarithmic Standard Deviation (σζ) of Particle Diameter Distribution" described in Columns 27 and 28 of U.S. Pat. No. 7,638,570. A specific measurement method will be detailed in Examples described later.

The mass average particle diameter (D50) of the water-absorbing resin in accordance with an embodiment of the present invention is preferably 50 μm to 700 μm, more preferably 50 μm to 500 μm, and even more preferably 100 μm to 400 μm. Further, the proportion of particles having a mass average particle diameter of less than 45 μm in 100 mass % of water-absorbing resin is preferably 40 mass % or less, more preferably 30 mass % or less, even more preferably 20 mass % or less, and particularly preferably 10 mass % or less. A water-absorbing resin having a mass average particle diameter of 50 μm or more generates less dust and provides good handleability. Further, a water-absorbing resin having a mass average particle diameter of 700 μm or less prevents or reduces a decrease in the speed at which a body fluid or the like such as urine and/or blood is absorbed by the water-absorbing resin and is thus suitable for use in, for example, a disposable diaper having a high water absorption speed.

<2-7> Number Average Particle Diameter

In a case where a water-absorbing resin is an aggregate-like particle (secondary particle), the number average particle diameter of primary particles (for example, spherical particles) constituting an aggregate (the aggregate-like particle) can be measured with use of an electron microscope. The number average particle diameter of the primary particles of the water-absorbing resin is preferably 5 μm to 800 μm, more preferably 8 μm to 500 μm, even more preferably 10 μm to 300 μm, still even more preferably 10 μm to 200 μm, and particularly preferably 30 μm to 200 μm. With regard to a method for measuring the number average particle diameter, an example of the method will be detailed in Examples.

<2-8>"Bulk Density"

The "bulk density" is measured in conformity with an EDANA method (ERT 460.2-02).

The bulk density of the water-absorbing resin in accordance with an embodiment of the present invention is preferably 0.68 g/cm$^3$ to 1.00 g/cm$^3$, preferably 0.69 g/cm$^3$ to 0.95 g/cm$^3$, and most preferably 0.68 g/cm$^3$ to 0.90 g/cm$^3$. A water-absorbing resin having a bulk density of 0.68 g/cm$^3$ to 1.00 g/cm$^3$ prevents or reduces a decrease in the speed at which a body fluid or the like such as urine and/or blood is absorbed by the water-absorbing resin and is thus suitable for use in, for example, a disposable diaper having a high water absorption speed.

<2-9> Liquid Permeability

The term "liquid permeability" as used in the present invention with respect to a water-absorbing resin refers to flowability of liquid between swollen gel particles under load or without load. The "liquid permeability" is measured typically as gel bed permeability (GBP). The "GBP" refers to a liquid permeability of a water-absorbing resin with respect to a 0.9 mass % aqueous sodium chloride solution under load or in freely swellable conditions, and is measured in conformity with the GBP testing method disclosed in International Publication No. WO 2005/016393. Note, however, that in an embodiment of the present invention, the particle size of the water-absorbing resin is measured without being classified into 300 μm or more and 600 μm or less. It is preferable that the liquid permeability is exhibited even in a state in which swelling of an absorbent core is prevented, and the GBP of the water-absorbing resin is preferably $5\times10^{-9}$ $cm^2$ or more, more preferably $10\times10^{-9}$ $cm^2$ or more, and even more preferably $15\times10^{-9}$ $cm^2$ or more.

<2-10> Swollen Gel Compressibility Rate

The "swollen gel compressibility rate" in the present invention is a novel physical property value that represents a thickness change (compressibility rate) of a swollen gel layer of a water-absorbing resin when a load is repeatedly applied to a swollen gel of the water-absorbing resin in a cell having a bottom portion in a mesh form. The "swollen gel compressibility rate" is measured by a method described later. A water-absorbing resin having a high "swollen gel compressibility rate" is such that a swollen gel layer of the water-absorbing resin is compressed when a load is repeatedly applied in, for example, a thin water-absorbing sheet for light incontinence. Therefore, a water-absorbing resin having a high "swollen gel compressibility rate" is preferable because swelling of an absorbent core is prevented even when used for a long period of time. The "swollen gel compressibility rate" is 3.0% or more, preferably 3.5% or more, more preferably 4.0% or more, even more preferably 4.5% or more, and particularly preferably 5.0% or more. The upper limit of the swollen gel compressibility rate is preferably 30% or less, 25% or less, and 20% or less in this order from the viewpoint of maintaining the absorption performance of a swollen gel layer of a water-absorbing resin.

<2-11> Thickness D1 of Swollen Gel Layer Before Compression

In the measurement of the "swollen gel compressibility rate", a smaller numerical value of a thickness D1 of the swollen gel layer before compression is more preferable from the viewpoint of preventing or reducing discomfort caused by excessive swelling of the absorbent core when the water-absorbing resin is used in the absorbent article. The thickness D1 of the swollen gel layer before compression is preferably 20 mm or less, more preferably 15 mm or less, and even more preferably less than 15 mm. The lower limit of D1 is not particularly limited and only needs to exceed 0 mm. The lower limit of D1 is preferably 5 mm or more, more preferably 10 mm or more, and even more preferably 12 mm or more.

<2-12> Thickness D2 of Swollen Gel Layer after Compression

In the measurement of the "swollen gel compressibility rate", a smaller numerical value of a thickness D2 of the swollen gel layer after compression is more preferable from the viewpoint of preventing or reducing discomfort caused by swelling of the absorbent core under a load (body weight) when the water-absorbing resin is used in the absorbent article. The "thickness D2 of the swollen gel layer after compression" is preferably 18 mm or less, more preferably 15 mm or less, and even more preferably less than 15 mm. The lower limit of D2 is not particularly limited and only needs to exceed 0 mm. The lower limit of D2 is preferably 5 mm or more, more preferably 10 mm or more, and even more preferably 12 mm or more.

Figure 2:
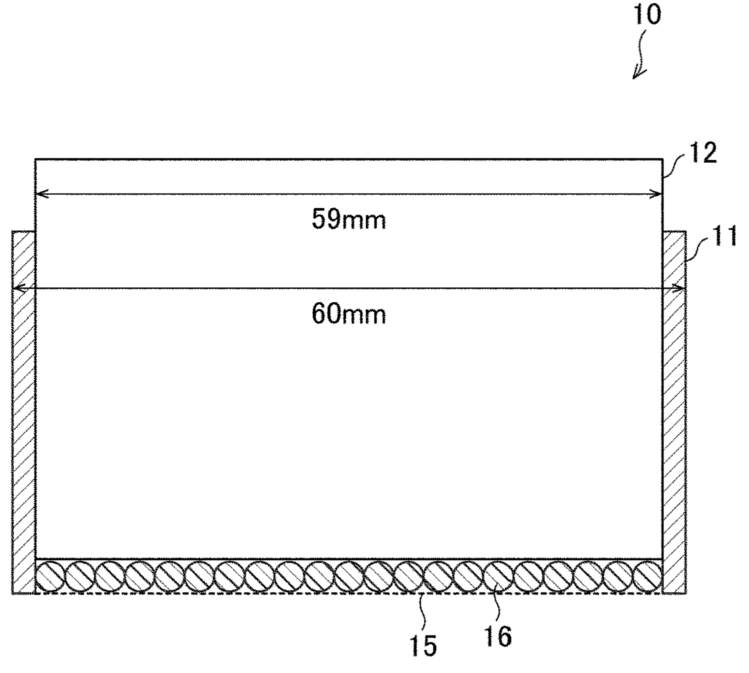
FIG. 2 is a cross-sectional view illustrating a part of the swollen gel compressibility rate measurement device.

A swollen gel compressibility rate measurement device (may be referred to simply as a measurement device) will be described with reference to FIGS. 1 and 2. FIG. 1 is a perspective view illustrating an external configuration of the swollen gel compressibility rate measurement device (measurement device) when viewed from one direction. FIG. 2 is a cross-sectional view illustrating a part of the swollen gel compressibility rate measurement device. As illustrated in FIG. 1, the swollen gel compressibility rate measurement device includes a cell 11, a piston 12, a petri dish 13, and a weight 14. As illustrated in FIG. 2, the inner diameter of the cell 11 is 60 mm, and the diameter of the piston 12 is 59 mm. In addition, as illustrated in FIG. 2, the cell 11 includes a bottom portion 15. The bottom portion 15 is a mesh made of stainless steel and is formed of a mesh with a mesh size of 36 μm (that is, 400 mesh).

A method for measuring the swollen gel compressibility rate will be described with reference to FIGS. 1 and 2. First, as illustrated in FIG. 2, a water-absorbing resin 16 is spread on the bottom portion 15 of the cell 11 having an inner diameter of 60 mm, the bottom portion 15 being in a mesh form. Next, as illustrated in FIG. 2, the piston 12 having a diameter of 59 mm is put into the cell 11 from above the spread water-absorbing resin 16. Next, as illustrated in FIG. 1, the cell 11 having the piston 12 and the water-water-absorbing resin 16 is placed in the petri dish 13 and is left to stand for 5 minutes. Here, although not illustrated in FIG. 1, a 0.9 mass % aqueous sodium chloride solution is present in the petri dish 13. Therefore, this operation allows the water-absorbing resin 16 in the cell 11 to absorb the 0.9 mass % aqueous sodium chloride solution for 5 minutes. Thus, the water-absorbing resin 16 forms a layer of a swollen gel (swollen gel layer). Note that, in FIG. 1, the weight 14 is illustrated on the piston 12 that is present inside the cell 11 placed in the petri dish 13. However, in actual measurement of the swollen gel compressibility rate, in placing the cell 11 having the piston 12 and the water-absorbing resin 16 in the petri dish 13 containing the 0.9 mass % aqueous sodium chloride solution, the weight 14 is not placed on the piston 12. As will be described later, the weight 14 is placed on the piston 12 in the cell 11 placed on a sieve. In FIG. 1, the state in which the weight 14 is placed on the piston 12 in the cell 11 placed on the sieve is illustrated, for convenience, with use of the piston 12 in the cell 11 placed in the petri dish 13.

After the water-absorbing resin 16 in the cell 11 has been caused to form the swollen gel layer, the thickness [mm] of the swollen gel layer is measured, and this thickness is assumed to be D1. Next, the cell 11 having the swollen gel layer of the water-absorbing resin 16 and the piston 12 is taken out from the petri dish 13 and placed on a sieve with a mesh size of 4750 μm. Subsequently, (1) an operation of allowing the cell 11 to stand still for 10 seconds with the weight 14 placed on the piston 12 in the cell 11 so that a load of 0.7 psi is applied to the swollen gel layer of the water-absorbing resin 16 and (2), after that, an operation of removing the weight 14 are repeated ten times. After that, the thickness [mm] of the swollen gel layer formed by the water-absorbing resin 16 is measured, and this thickness is assumed to be D2.

Subsequently, from D1 and D2, the swollen gel compressibility rate is calculated based on the following formula (1):

$$\text{Swollen gel compressibility rate [\%]} = (D1 - D2)/D1 \times 100. \quad \text{(Formula 1)}$$

<2-13> Additive to be Contained

In an embodiment of the present invention, a water-absorbing resin (water-absorbing composition) can contain an additive for allowing the water-absorbing resin to exhibit various functions. Specifically, examples of such an additive encompass a surfactant, a compound having a phosphorus atom, an oxidizer, an organic reducing agent, an inorganic reducing agent, water-insoluble inorganic fine particles, a chelating agent, a polyvalent metal salt, organic powder such as metallic soap, a deodorizing agent, an antibacterial agent, pulp, thermoplastic fibers, and the like. An amount of the additive used (added) is set as appropriate according to an application for which a resulting water-absorbing resin is used, and is 5 mass % or less, preferably 3 mass % or less, and more preferably 1 mass % or less, in 100 mass % of the water-absorbing resin (for example, water-absorbing resin powder, powdery water-absorbing resin composition, and the like). A lower limit of the amount of the additive used (added) is 0.001 mass % or more and preferably 0.01 mass % or more relative to the water-absorbing resin (for example, water-absorbing resin powder). Note that the water-insoluble inorganic fine particles are exemplified by a compound disclosed in "<5> Water-insoluble inorganic fine particles" of International Publication No. WO 2011/040530, and such a compound can be suitably employed in an embodiment of the present invention. In addition, the polyvalent metal salt is preferably a water-soluble polyvalent metal salt and more preferably a water-soluble aluminum salt. Examples of the water-soluble aluminum salt encompass aluminum sulfate.

<3> Method for Producing Water-Absorbing Resin

A method for producing the water-absorbing resin in accordance with an embodiment of the present invention may use any of the following: aqueous solution polymerization, reversed phase suspension polymerization, vapor phase droplet polymerization, other polymerization methods, and the like. From the viewpoint of ease of control of the physical properties of the water-absorbing resin in accordance with an embodiment of the present invention, it is preferable to employ a reversed phase suspension polymerization method. For the method for producing the water-absorbing resin in accordance with an embodiment of the present invention, the following will describe the reversed phase suspension polymerization method as an example. A preferable aspect of the method for producing the water-absorbing resin in accordance with an embodiment of the present invention will be described by taking, as an example, in particular, a production method including a step of separating a gel obtained by reversed phase suspension polymerization, a gel sizing step, a hydrogel drying step (preferably hot air drying), and a surface-crosslinking step (preferably powder surface treatment), unlike general reversed phase suspension polymerization including an azeotropic dehydration step in a hydrophobic organic solvent after polymerization and/or a surface-crosslinking step in a dispersion system.

The method for producing the water-absorbing resin in accordance with an embodiment of the present invention is not particularly limited, and preferably includes a polymerization step of obtaining a hydrogel polymer by, in a state in which droplets containing a monomer are dispersed or suspended in a hydrophobic organic solvent, polymerizing the monomer.

Preferable as the method for producing a water-absorbing resin (polymerization method) is, for example, a method of obtaining a hydrogel polymer by, in a state in which droplets containing a monomer are dispersed or suspended in a liquid phase composed of a hydrophobic organic solvent, polymerizing the monomer, in other words, a method of obtaining a hydrogel polymer by reversed phase suspension polymerization. A method for the reversed phase suspension polymerization may be a batch-type method or a continuous-type method. A batch-type production method is a production method in which an aqueous monomer solution is added or dropped into a hydrophobic organic solvent in a reaction apparatus and mixed to disperse or suspend droplets of the aqueous monomer solution in the hydrophobic organic solvent, and then polymerization of the monomer is carried out to obtain a hydrogel polymer. On the other hand, a continuous-type production method is a method in which an aqueous monomer solution is continuously fed to a hydrophobic organic solvent in a reaction apparatus to disperse or suspend droplets of the aqueous monomer solution in the hydrophobic organic solvent, the monomer is then polymerized, and a hydrogel polymer formed by a polymerization reaction and the hydrophobic organic solvent are continuously discharged from the reaction apparatus. A preferable embodiment of the present invention is batch-type reversed phase suspension polymerization. In the method for producing the water-absorbing resin in accordance with an embodiment of the present invention, a separation step of separating the hydrogel polymer obtained in the polymerization step from the hydrophobic organic solvent may be provided.

A method for producing a water-absorbing resin in accordance with an embodiment of the present invention, for example, includes: any aqueous monomer solution preparation step; any dispersion step; a polymerization step; any separation step; any gel sizing step; a drying step; and a hydrophilization treatment step. Further, the method can optionally include, after the drying step, a cooling step, a pulverizing step, a classification step, a surface-crosslinking step, a hydration (re-moistening) step, an other additive addition step, a sizing step, a fine powder removal step, a granulation step, a fine powder reuse step, and the like. Further, the method may further include a conveying step, a storing step, a packing step, a reserving step, and the like.

The individual steps will be described below.

<3-1> Aqueous Monomer Solution Preparation Step

The aqueous monomer solution is an aqueous solution that contains a monomer which serves as a raw material for a water-absorbing resin, and is a solution to be dispersed or suspended in a hydrophobic organic solvent in order to carry out reversed phase suspension polymerization.

As the solvent of the aqueous monomer solution, water or a mixture of water and a water-soluble organic solvent (for example, alcohol or the like) is suitably used. The solvent of the aqueous monomer solution is even more preferably water. In a case where the solvent is a mixture of water and a water-soluble organic solvent, the water-soluble organic solvent (for example, alcohol or the like) accounts for preferably 30 mass % or less and more preferably 5 mass % or less of the mixture (100 mass %).

As the monomer, a water-soluble ethylenically unsaturated monomer is preferably used. Examples of the water-soluble ethylenically unsaturated monomer encompass: acid group-containing unsaturated monomers such as (meth)acrylic acid, maleic acid (anhydride), itaconic acid, cinnamic acid, vinylsulfonic acid, allyltoluene sulfonic acid, vinyltoluene sulfonic sulfonic acid, 2-(meth)acrylamide-2-methylpropane sulfonic acid, 2-(meth)acryloylethane sulfonic acid, 2-(meth)acryloylpropane sulfonic acid, 2-hydroxyethyl (meth)acrylate, 2-hydroxypropyl (meth)acrylate, 2-hydroxyethyl (meth)acryloyl phosphate, methoxypolyethylene glycol (meth)acrylate, and polyethylene glycol mono (meth)acrylate; amide group-containing unsaturated monomers such as (meth)acrylamide, N-ethyl (meth)acrylamide, N,N-dimethyl (meth)acrylamide, N-n-propyl (meth)acrylamide, N-isopropyl (meth)acrylamide, vinylpyridine, N-vinylpyrrolidone, N-acrylloyl piperidin, N-acrylloyl pyrrolidine, and N-vinylacetamide; amino group-containing unsaturated monomers such as N, N-dimethylaminoethyl (meth)acrylate, N,N-dimethylaminopropyl (meth)acrylate, N,N-dimethylaminopropyl (meth)acrylamide, and N, N-diethylaminoethyl (meth)acrylate; mercapto group-containing unsaturated monomers; phenolic hydroxyl group-containing unsaturated monomers; lactam group-containing unsaturated monomers such as N-vinylpyrrolidone; and the like.

Note that, in a case where the water-soluble ethylenically unsaturated monomer is used, a polymerization inhibitor may be added, as necessary, to the aqueous monomer solution, in consideration of stability of the water-soluble ethylenically unsaturated monomer.

In a case where an acid group-containing unsaturated monomer having an acid group such as a carboxyl group among the water-soluble ethylenically unsaturated monomers is used to produce a water-absorbing resin, a neutralized salt obtained by neutralizing the acid group can be used. In this case, a salt (neutralized salt) of the acid group-containing unsaturated monomer is preferably a salt with a monovalent cation, more preferably at least one salt selected from the group consisting of an alkali metal salt, an ammonium salt, and an amine salt, further preferably an alkali metal salt, even further preferably at least one salt selected from the group consisting of a sodium salt, a lithium salt, and a potassium salt, and particularly preferably a sodium salt.

Among these water-soluble ethylenically unsaturated monomers, from the viewpoint of the water absorption performance of a resulting water-absorbing resin, the water-soluble ethylenically unsaturated monomer is preferably an acid group-containing unsaturated monomer and/or a salt thereof, more preferably (meth)acrylic acid (salt), maleic acid (anhydride) (salt), itaconic acid (salt), and/or cinnamic acid (salt), even more preferably (meth)acrylic acid (salt), and particularly preferably acrylic acid (salt).

In a case where an acid group-containing unsaturated monomer is used as the monomer, the acid group-containing unsaturated monomer and a neutralized salt of the acid group-containing unsaturated monomer are preferably used in combination from the viewpoint of water absorption performance of a resulting water-absorbing resin. In a case where an acid group-containing unsaturated monomer and a neutralized salt of the acid group-containing unsaturated monomer are used in combination, the number of moles of the neutralized salt relative to the total number (100 mol %) of moles of the acid group-containing unsaturated monomer and the neutralized salt thereof (hereinafter, referred to as "neutralization ratio") is preferably 40 mol % or more, more preferably 40 mol % to 95 mol %, further preferably 50 mol % to 90 mol %, even further preferably 55 mol % to 85 mol %, and particularly preferably 60 mol % to 80 mol %, from the viewpoint of water absorption performance.

In the production method in accordance with an embodiment of the present invention, in the preparation of the aqueous monomer solution, any one of the monomers listed above as examples may be used solely, or any two or more of the monomers may be mixed as appropriate and used. In addition, a monomer other than the monomers listed above as examples may be further mixed and used with respect to the monomer(s) listed above as examples, provided that the object of an embodiment of the present invention is achieved.

In a case where two or more of the monomers are used in combination in the preparation of the aqueous monomer solution, it is preferable that the monomers used for the polymerization include (meth)acrylic acid (salt) as a main component. In this case, from the viewpoint of the water absorption performance of a resulting water-absorbing resin, the proportion of the (meth)acrylic acid (salt) to the entire monomer (100 mol %) used for the polymerization is normally not less than 50 mol % or more, preferably 70 mol % or more, more preferably 80 mol % or more, and further preferably 90 mol % or more (the upper limit is 100 mol %).

In the preparation of the aqueous monomer solution, an internal crosslinking agent can be used as necessary. The internal crosslinking agent is exemplified by a conventionally known internal crosslinking agent having two or more polymerizable unsaturated groups two or more reactive groups within one molecule thereof. Examples of the internal crosslinking agent encompass N, N'-methylene bis (meth)acrylamide, (poly)ethylene glycol di(meth)acrylate, (poly)propylene glycol di(meth)acrylate, trimethylol propane tri(meth)acrylate, trimethylol propane di(meth)acrylate, glycerin tri(meth)acrylate, glycerin acrylate methacrylate, ethylene oxide-modified trimethylol propane tri(meth) acrylate, pentaerythritol tetra(meth)acrylate, dipentaerythritol hexa(meth)acrylate, triallyl cyanurate, triallyl isocyanurate, triallyl phosphate, triallylamine, poly (meth)allyloxy alkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl (meth)acrylate, and the like. Only one of these internal crosslinking agents may be used solely, or two or more thereof may be used in combination.

The amount of the internal crosslinking agent used is determined as appropriate in accordance with the physical properties of a desired water-absorbing resin and is normally 0.0001 mol % to 5 mol %, more preferably 0.001 mol % to 3 mol %, and even more preferably 0.005 mol % to 1.5 mol %, relative to the entire monomer (100 mol %) used for polymerization.

In addition, substances (hereinafter, referred to as "other substances") examples of which will be listed below can also be added to the aqueous monomer solution.

Specific examples of the other substances encompass: chain transfer agents such as thiols, thiolic acids, secondary alcohols, amines, and hypophosphites; foaming agents such as carbonates, bicarbonates, azo compounds, and bubbles; chelating agents such as metal salts of ethylenediamine tetraacetic acid, and metal salts of diethylenetriamine pentaacetic acid; polyacrylic acid (salt) and crosslinked products thereof; starch; cellulose; starch-cellulose derivatives; hydroxyethyl cellulose; polyvinyl alcohol; and the like. One of the other substances may be used solely, or two or more thereof may be used in combination.

The amount of the other substances used is not particularly limited, and the total concentration of the other substances is preferably 10 mass % or less, more preferably 1 mass % or less, and even more preferably 0.1 mass % or less, relative to the entire monomer (100 mass %) used for the polymerization.

A case where (a) polyacrylic acid (salt) and crosslinked products thereof, (b) starch, (c) cellulose, (d) starch-cellulose derivatives, and/or (e) polyvinyl alcohol is/are used as the other substances will be described. The total concentration of these (a) polyacrylic acid (salt) and crosslinked products thereof, (b) starch, (c) cellulose, (d) starch-cellulose derivatives, and (e) polyvinyl alcohol is not particularly limited and is preferably 30 mass % or less, more preferably 20 mass % or less, and even more preferably 10 mass % or less, relative to the whole monomer (100 mass %) used for polymerization.

Further, dissolved oxygen in the aqueous monomer solution may be reduced by temperature increase or substitution with an inert gas.

"Polymerization Initiator"

In the preparation of the aqueous monomer solution, a polymerization initiator may be used. Note that, in a case where a polymerization initiator is used in the preparation of an aqueous monomer solution, gelation of the aqueous monomer solution and/or increase in viscosity thereof may occur. Thus, for the addition of the polymerization initiator to the aqueous monomer solution, for example, the following (1), (2), and (3), are preferably carried out: (1) the addition of the polymerization initiator is carried out immediately before the aqueous monomer solution is dispersed and/or suspended in a hydrophobic organic solvent; (2) the aqueous monomer solution is cooled and is mixed with the polymerization initiator at a temperature (for example, 20° C. or lower, preferably around 0° C.) lower than normal temperature; and (3) the dispersion step is carried out while the aqueous monomer solution and the polymerization initiator are mixed in a static mixer. As the polymerization initiator, a pyrolytic polymerization initiator is preferably used. The pyrolytic polymerization initiator refers to a compound that is decomposed by heat to generate radicals. From the viewpoint of storage stability of the pyrolytic polymerization initiator and/or production efficiency of a water-absorbing resin, preferably used as the polymerization initiator is a water-soluble compound having a 10-hour half-life temperature of preferably 0° C. to 120° C., more preferably 30° C. to 100° C., and even more preferably 50° C. to 80° C.

From the viewpoint of handleability and/or physical properties of a water-absorbing resin, the polymerization initiator is preferably a water-soluble polymerization initiator, and more preferably a water-soluble radical polymerization initiator.

Examples of the water-soluble radical polymerization initiator encompass: persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butylperoxyacetate, t-butylperoxyisobutyrate, t-butylperoxypivalate, and hydrogen peroxide; water-soluble azo compounds such as 2,2'-azobis(2-amidinopropane) dihydrochloride, 2,2'-azobis[2-(N-phenylamidino) propane]dihydrochloride, and 2,2'-azobis[2-(2-imidazolin-2-yl)propane]dihydrochloride; and the like. As the polymerization initiator, one of these polymerization initiators may be used solely, or two or more thereof may be used in combination. Among these polymerization initiators, persulfates and/or water-soluble azo compounds are preferably used, sodium persulfate, potassium persulfate, ammonium persulfate, and/or 2,2'-azobis(2-amidinopropane) dihydrochloride is/are more preferably used, and sodium persulfate is even more preferably used.

The amount of the pyrolytic polymerization initiator used is set as appropriate in accordance with, for example, the types of the monomer and of the polymerization initiator and is not particularly limited. From the viewpoint of production efficiency, the amount of the pyrolytic polymerization initiator used is preferably 0.001 g/mol or more, more preferably 0.005 g/mol or more, and even more preferably 0.010 g/mol or more, relative to the entire monomer (1 mole) used for polymerization. Further, from the viewpoint of improvement in water absorption performance of a water-absorbing resin, the amount of the pyrolytic polymerization initiator used is preferably 2 g/mol or less and more preferably 1 g/mol or less, relative to the entire monomer (1 mole) used for polymerization.

In addition, if necessary, the pyrolytic polymerization initiator can be used in combination with another polymerization initiator such as a photolytic polymerization initiator. Specific examples of the photolytic polymerization initiator encompass benzoin derivatives, benzyl derivatives, acetophenone derivatives, benzophenone derivatives, and the like.

In addition, the pyrolytic polymerization initiator and a reducing agent can be used in combination as a redox polymerization initiator. In the redox polymerization initiator, the pyrolytic polymerization initiator functions as an oxidizing agent. The reducing agent to be used is not particularly limited, and examples of the reducing agent encompass: (bi)sulfites such as sodium sulfite and sodium hydrogen sulfite; reducing metal salts such as a ferrous salt; L-ascorbic acid (salt); amines; and the like.

"Concentration of Monomer in Aqueous Monomer Solution"

In an embodiment of the present invention, the concentration of a monomer in an aqueous monomer solution (100 mass %) is selected according to, for example, the types of a selected monomer and of a selected hydrophobic organic solvent. In terms of production efficiency, the lower limit of the concentration of the monomer in the aqueous monomer solution (100 mass %) is preferably 10 mass % or more, more preferably 20 mass % or more, and even more preferably 30 mass % or more in the aqueous monomer solution, and the upper limit thereof is preferably 100 mass % or less, more preferably 90 mass % or less, even more preferably 80 mass % or less, and further more preferably 70 mass % or less.

It is also possible to blend an additive such as an internal crosslinking agent, a surfactant, a density adjusting agent, a thickener, and a chelating agent into the aqueous monomer solution, provided that the object of an embodiment of the present invention is not impaired. Note that the type of the additive and the amount of the additive added can be selected as appropriate depending on a combination of the monomer used and the hydrophobic organic solvent used.

<3-2> Dispersion Step

The dispersion step is a step of dispersing or suspending droplets containing a monomer (for example, droplets of an aqueous monomer solution) in a hydrophobic organic solvent. Note that, hereinafter, in a case where the term "dispersion" is simply described, the dispersion conceptually encompasses suspension. More specifically, the aqueous monomer solution is added to a hydrophobic organic solvent, mixed, and stirred so that the droplets containing the monomer are dispersed in the hydrophobic organic solvent. For example, a stirring apparatus provided with a stirring blade (such as a propeller blade, a paddle blade, an anchor blade, a turbine blade, a Phaudler blade, a ribbon blade, and a flat plate blade) may be used in the dispersion step. In a case where a stirring apparatus having such a stirring blade is used, a dispersed droplet diameter (droplet diameter of a dispersed aqueous monomer solution) can be adjusted depending on the type of the stirring blade, a blade diameter, the number of rotations, and the like. In a case where batch-type reversed phase suspension polymerization is carried out, the stirring apparatus can be particularly suitably used. Further, a dispersion can also be obtained by a method described in, for example, International Publication No. WO 2009/025235 and International Publication No. WO 2013/018571. In a case where the continuous-type reversed phase suspension polymerization is carried out, the dispersion step is preferably such that the aqueous monomer solution and the hydrophobic organic solvent are continuously and separately supplied to the dispersion apparatus, and droplets containing the monomer and dispersed in the hydrophobic organic solvent are prepared.

In a case where the continuous-type reversed phase suspension polymerization is carried out, examples of the dispersion apparatus used in the dispersion step encompass: a spray nozzle; a high-speed rotary shear type stirrer (such as a rotary mixer type, a turbo mixer type, a disk type, and a double cylinder type); a cylindrical nozzle; an orifice plate in which a large number of holes are directly provided in the plate; a centrifugal atomizer; and the like. However, there is no particular limitation.

"Hydrophobic Organic Solvent"

A preferable hydrophobic organic solvent is exemplified by at least one organic solvent selected from the group consisting of aliphatic hydrocarbons, alicyclic hydrocarbons, aromatic hydrocarbons, and halogenated hydrocarbons. Specific examples of the hydrophobic organic solvent encompass: aliphatic hydrocarbons such as n-pentane, n-hexane, n-heptane, and n-octane; alicyclic hydrocarbons such as cyclohexane, methylcyclohexane, cyclooctane, and decalin; aromatic hydrocarbons such as benzene, toluene, and xylene; and halogenated hydrocarbons such as chlorobenzene, bromobenzene, carbon tetrachloride, and 1,2-dichloroethane. Among these hydrophobic organic solvents, from the viewpoint of ease of availability and quality stability, the hydrophobic organic solvent is preferably one or more selected from the group consisting of n-hexane, n-heptane, and cyclohexane. The hydrophobic organic solvent can also be used as a mixture solvent in which two or more of these hydrophobic organic solvents are mixed.

In an embodiment of the present invention, a dispersion aid such as a surfactant and/or a polymer additive may be added, as necessary, to the hydrophobic organic solvent, provided that the object of an embodiment of the present invention is not impaired. The type of dispersion aid is selected as appropriate depending on a combination of the hydrophobic organic solvent and the monomer to be used, and examples of the dispersion aid that can be used encompass the following surfactants and polymer additives.

Specific examples of the surfactant encompass sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hardened castor oil, alkylallylformaldehyde-condensed polyoxyethylene ethers, polyoxyethylene polyoxypropylene block copolymers, polyoxyethylene polyoxypropyl alkyl ethers, polyethylene glycol fatty acid esters, alkyl glucosides, N-alkyl gluconamides, polyoxyethylene fatty acid amides, polyoxyethylene alkylamines, phosphates of polyoxyethylene alkyl ethers, phosphates of polyoxyethylene alkyl aryl ethers, and the like. One of these surfactants may be used solely, or two or more thereof may be used in combination. Further, a polymerizable surfactant having polymerizability can also be used. The polymerizable surfactant is, specifically, exemplified by a compound having the following structure:

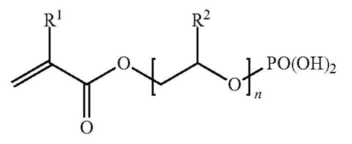

Note that, in the formula, $R^1$ and $R^2$ are hydrogen, methyl, or ethyl independently of each other, and n means an integer of 3 to 20.

Among the above-described surfactants, fatty acid esters such as sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, and polyethylene glycol fatty acid esters are preferable. Among them, sucrose fatty acid esters are preferable.

Further, an HLB value of the surfactant used in an embodiment of the present invention is in the range of preferably 1 to 20, more preferably 1 to 10, and even more preferably 3 to 6.

Specific examples of the polymer additive encompass maleic anhydride-modified polyethylene, maleic anhydride-modified polypropylene, maleic anhydride-modified ethylene-propylene copolymer, maleic anhydride-modified ethylene-propylene-diene terpolymer (EPDM), maleic anhydride-modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylic acid copolymer, ethyl cellulose, hydroxyethyl cellulose, and the like. Among them, from the viewpoint of dispersion stability of the aqueous monomer solution, maleic anhydride-modified polyethylene, maleic anhydride-modified polypropylene, maleic anhydride-modified ethylene-propylene copolymer, maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and oxidized ethylene-propylene copolymer are preferable. One of these polymer additives may be used solely, or two or more thereof may be used in combination. In addition, these polymer additives and the surfactant may be used in combination. Above all, it is preferable to use the polymer additive, and it is more preferable to use a maleic anhydride-modified ethylene-propylene copolymer. Further, in another preferred embodiment, the polymer additive is used solely without using the surfactant.

The amount of the dispersion aid used is set as appropriate in accordance with, for example, the polymerization form and the types of the aqueous monomer solution and of the hydrophobic organic solvent. Specifically, the concentration of the dispersion aid in the hydrophobic organic solvent (100 mass %) is preferably 0.0001 mass % to 2 mass % and more preferably 0.0005 mass % to 1 mass %.

<3-3> Polymerization Step

The polymerization step is a step of polymerizing a monomer in droplets containing the monomer obtained in the dispersion step so that a hydrogel polymer (hereinafter also referred to simply as hydrogel) is obtained.

"Reaction Apparatus"

As the reaction apparatus to be used in the polymerization step, the dispersion apparatus used in the dispersion step may be used as it is, or a different apparatus may be used. In the case of the batch-type reversed phase suspension polymerization, the apparatus used in the dispersion step can be used as it is as the reaction apparatus. This is suitable in terms of workability. In a case where the reaction apparatus is an apparatus different from the dispersion apparatus, the dispersion liquid of the monomer obtained in the dispersion step is supplied to the reaction apparatus.

Further, the shape of the reaction apparatus in which the polymerization reaction is carried out is not particularly limited, and a known reaction apparatus can be used. As described above, the stirring apparatus that can be suitably used in the dispersion step can also be suitably used in the polymerization reaction. In the case of the continuous-type production method, the shape of the reaction apparatus is preferably a shape that allows the monomer (aqueous solution) to undergo polymerization reaction while moving, as a droplet-like dispersed phase, in a hydrophobic organic solvent which is a continuous phase formed in this reaction apparatus. Examples of such a reaction apparatus encompass a reaction apparatus in which a tubular reaction tube is disposed in a vertical fashion, a horizontal fashion, or a spiral fashion. In this aspect, since the monomer (aqueous solution) is supplied into the hydrophobic organic solvent that moves in the reaction unit (reaction tube), the droplets composed of the aqueous monomer solution move together with the hydrophobic organic solvent without staying. This prevents contact between monomer reactants having different polymerization rates.

Further, the reaction apparatus may be provided with a temperature adjustment means (for example, a heating means) so that the continuous phase inside the reaction apparatus can be heated and/or cooled from the outside, if necessary.

"Polymerization Temperature"

A polymerization temperature, which is a reaction temperature in the polymerization step, is set as appropriate depending on the type and/or amount of the polymerization initiator to be used, and is preferably 20° C. to 100° C. and more preferably 40° C. to 90° C. The polymerization temperature of higher than 100° C. is not preferable because such a polymerization temperature causes a rapid polymerization reaction. Note that the polymerization temperature means the temperature (hereinafter referred to as "Td") of the hydrophobic organic solvent which serves as a dispersion medium.

In the polymerization step, the monomer (aqueous solution) is dispersed in the hydrophobic organic solvent in the form of droplets. Thus, the temperature of the aqueous monomer solution rapidly increases due to heat transfer from the hydrophobic organic solvent. In a case where the polymerization initiator contained in the droplets is a pyrolytic polymerization initiator, the pyrolytic polymerization initiator is decomposed with the increase in temperature, so that radicals are generated. Then, the polymerization reaction is initiated by the generated radicals, and a hydrogel is formed as the polymerization reaction progresses.

In the case of the continuous-type production method, the formed hydrogel is moved inside the reaction apparatus by the moving continuous phase, and is discharged from the reaction apparatus together with the hydrophobic organic solvent that forms the continuous phase.

In a case where the aqueous monomer solution contains a pyrolytic polymerization initiator, the Td is preferably 70° C. or higher, more preferably 75° C. or higher, and even more preferably 80° C. or higher, from the viewpoint of the polymerization rate. The upper limit of Td is not particularly limited and is selected as appropriate, from the viewpoint of safety, in a range which does not exceed the boiling point of the hydrophobic organic solvent that forms the continuous phase.

"Multi-Stage Reversed Phase Suspension Polymerization"

In the production method in accordance with an present invention, multi-stage embodiment of the polymerization may be carried out from the viewpoint of obtaining an appropriate aggregated particle diameter (particle diameter of an aggregate-like particle). Specifically, the multi-stage polymerization can be carried out, for example, by, after the end of a first-stage polymerization step, further adding the aqueous monomer solution and carrying out a polymerization reaction. In the multi-stage polymerization, a reaction solution may be stirred as appropriate.

"Inorganic Fine Particles"

In the production method in accordance with an embodiment of the present invention, inorganic fine particles may be added to the hydrogel polymer during the polymerization and/or after the end of the polymerization, from the viewpoint of obtaining an appropriate aggregated particle diameter.

Examples of the inorganic fine particles that can be used in an embodiment of the present invention encompass silicon dioxide, aluminum oxide, titanium dioxide, calcium phosphate, calcium carbonate, magnesium phosphate, calcium sulfate, diatomaceous earth, bentonite, zeolite, other metal oxides, and the like. As the inorganic fine particles, silicon dioxide, aluminum oxide, and titanium dioxide in particular, are preferable.

Good results can be obtained when the amount of the inorganic fine particles added is such that the inorganic fine particles are used in a proportion of generally 0.001 parts by mass to 1 part by mass, preferably 0.001 parts by mass to 0.5 parts by mass, relative to the hydrogel polymer (100 parts by mass). The amount of the inorganic fine particles added falling within this range is preferable since the effect produced by the addition of the inorganic fine particles is efficiently exhibited, and the influence of the inorganic fine particles on the water absorption performance is small.

<3-4> Separation Step

The separation step is a step of separating the hydrogel polymer obtained in the polymerization s from the hydrophobic organic solvent. The type and structure of the apparatus to be used in the separation step are not particularly limited. For example, a known apparatus used for filtration, sedimentation, centrifugation, squeezing, and the like can be used. Further, separation of the hydrogel polymer from the hydrophobic organic solvent may be carried out by distillation performed through the heating of a mixture of the hydrogel polymer and the hydrophobic organic solvent under normal pressure or reduced pressure with use of the stirring apparatus having a stirring blade and used in the polymerization step. In the batch-type reversed phase suspension polymerization, distillation under normal pressure or reduced pressure is suitably performed.

<3-5> Gel Sizing Step

In the gel sizing step, the hydrogel polymer separated from the hydrophobic organic solvent in the separation step is sized with use of a gel sizing apparatus having an extrusion action unit and a porous plate. As a result, a sized hydrogel polymer (hereinafter, the hydrogel after gel sizing is referred to as sized gel) is obtained. The gel sizing step is an optional step. Having the gel sizing step makes it easy to control the compressibility rate (swollen gel compressibility rate) of a swollen gel layer of a water-absorbing resin.

The hydrogel polymer used in the gel sizing step is in the form of a single particle of a spherical gel or in the form of an aggregate of spherical gels. The lower limit of the average particle diameter of the hydrogel polymer is not particularly limited and is preferably 0.01 mm or more, more preferably 0.03 mm or more, even more preferably 0.05 mm or more, still more preferably 0.1 mm or more. The upper limit of the average particle diameter of the hydrogel polymer is also not particularly limited and is preferably 20 mm or less and more preferably 10 mm or less.

Further, in the case where the hydrogel polymer is in the form of a single particle, the particle diameter of the spherical gel is referred to as a primary particle diameter of the hydrogel polymer. In the case where the hydrogel polymer is in the form of an aggregate, the particle diameter of each spherical gel constituting the aggregate is referred to as a primary particle diameter of the hydrogel polymer. In an embodiment of the present invention, an average primary particle diameter of the hydrogel polymer is not particularly limited, and is preferably 5 μm to 2000 μm, more preferably 5 μm to 1000 μm, even more preferably 5 μm to 800 μm, still more preferably 8 μm to 500 μm, further more preferably 10 μm to 300 μm, and particularly preferably 10 μm to 200 μm, from the viewpoint of preventing the generation of fine powder in the drying step.

Note that an apparatus having a cutter may be installed in front of the gel sizing apparatus having the extrusion action unit and the porous plate to crush large aggregates of the hydrogel polymer.

"Temperature of Hydrogel"

The lower limit of the temperature of the hydrogel put into (charged into) the gel sizing apparatus is not particularly limited, and is preferably 80° C. or higher and more preferably 90° C. or higher, from the viewpoint of granulation efficiency and prevention of damage to the hydrogel. The upper limit of the temperature of the hydrogel at the charge into the gel sizing apparatus is not particularly limited, and is generally 100° C. or lower.

"Gel Sizing Apparatus"

In the present specification, "gel sizing" means an operation of extruding a wet powder mass (for example, a hydrogel) into a columnar shape through a small hole of a porous plate to prepare grains having a substantially uniform shape and size from a wet powder-like raw material. That is, with use of the porous plate, hydrogels in the form of a coarse aggregate resulting from excessive aggregation in a solvent separation step which is a previous step are crushed, and hydrogels in the form of a single particle having a small particle diameter are appropriately aggregated. Therefore, the gel sizing step makes it possible to obtain a hydrogel (sized gel) having a granulation shape and having a relatively uniform particle diameter. The sized gel may contain a hydrogel in the form of a single particle.

As the "gel sizing apparatus having an extrusion action unit and a porous plate" used in the gel sizing step is not particularly limited, provided that the gel sizing apparatus is an apparatus (for example, an extruder) having an extrusion action unit and a porous plate (die or screen), the extrusion action unit generally having an extrusion member for extruding and supplying the contents toward the porous plate, and being capable of preparing grains of a certain size by extruding a material from the porous plate. Further, a configuration may be employed in which a plurality of the above-described apparatus are prepared, and the plurality of apparatuses are placed in series and used.

Further, the shape of the hole of this porous plate (die or screen) is not particularly limited, and it is possible to freely select a shape suitable for use, including a perfect-circular shape, an elliptical shape, a polygonal shape such as a hexagonal shape, a triangular shape, and the like. From the viewpoint of sizing strength, a perfect-circular shape and an elliptical shape are preferable. The hole diameter of the hole of the porous plate is also not particularly limited and is preferably 1.5 mm or less, more preferably 1.0 mm or less, and even more preferably 0.8 mm or less. A hole diameter equal to or lower than such an upper limit prevents or reduces an increase in the size of a resulting sized gel more than necessary, and makes it possible to reduce the amount of fine powder generated during drying with use of a stirring-type dryer in a downstream step. The hole diameter is preferably 0.3 mm to 1.5 mm and more preferably 0.3 mm to 0.8 mm. With the porous plate having a pore diameter of 0.3 mm or more, it is possible to efficiently carry out extrusion when an extrusion operation is carried out.

Note that the hole diameter is defined as follows. First, in a case where the hole does not have a perfect-circular shape, a geometric mean value of a minor axis of the hole and a major axis thereof is adopted as the hole diameter. Further, in a case where the holes of the porous plate have different hole diameters, the hole diameters of all the holes are calculated, and a geometric mean value of the hole diameters is adopted as the hole diameter of the holes of the porous plate. Furthermore, in a case where the porous plate has varying hole diameters in a distance between an extrusion action unit side of the porous plate and a side opposite to the extrusion action unit side (the hole diameter varies in the thickness direction of the porous plate), a smallest hole diameter value among the hole diameters is adopted.

In the gel sizing step, an additive may be further added to the hydrogel polymer. Examples of the additive that can be added in the gel sizing step encompass a polymerization initiator, an oxidizing agent, a reducing agent, a chelating agent, a thickener, a surfactant, a crosslinking agent, an acid, a base, a foaming agent, organic or inorganic fine particles, a polyvalent metal, and the like. Among them, preferable as an additive that can control the degree of aggregation are, for example, a thickener such as starch, cellulose, a starch-cellulose derivative, and polyvinyl alcohol, a surfactant, fine powder of a water-absorbing resin, a crosslinking agent, a polyvalent metal salt, and the like. The polyvalent metal salt is preferably a water-soluble polyvalent metal salt and more preferably a water-soluble aluminum salt. Examples of the water-soluble aluminum salt encompass aluminum sulfate.

<3-6> Drying Step

The drying step is a step of drying a hydrogel. In a case where the gel sizing step is carried out, the drying step is a step of drying a sized gel. In an embodiment of the present invention, a drying method in the drying step is not particularly limited. As the drying method, azeotropic dehydration in a hydrophobic dispersing solvent used in the conventional reversed phase suspension polymerization may be employed. As a more suitable method for obtaining the water-absorbing resin in accordance with an embodiment of the present invention by reversed phase suspension polymerization, both stirring drying and static drying can preferably be employed instead of azeotropic dehydration. In an embodiment of the present invention, stirring drying is further preferably employed as the drying step, in order to maintain the particle diameter of the gel controlled in the gel sizing step. In the drying step, an apparatus equipped with a heating means may be used to heat the hydrogel. Further, in a case where stirring drying is employed, a rotary dryer equipped with a rotary container may be used as a drying apparatus.

The dried polymer composed of particles obtained in the drying step can be directly used as a water-absorbing resin for each application. Further, in a case where a water-absorbing resin is produced by this production method, the dried polymer obtained in the drying step can be subjected to the surface-crosslinking step described later. In this case, the dried polymer to be subjected to the surface-crosslinking step described later is also referred to as "water-absorbing resin powder" for convenience.

"Additive"

An additive may be added to a hydrogel, provided that the effect of an embodiment of the present invention is not impaired. The additive may be added to the hydrogel during heating of the hydrogel by the heating means and/or during stirring (rotation) of the hydrogel by the rotary container. The additive may be added to the hydrogel before the drying step (before heating of the hydrogel by the heating means and/or before stirring (rotation) of the hydrogel by the rotary container). Furthermore, the additive may be added to the hydrogel in any step previous to the drying step. With the additive, excessive adhesion between hydrogels during drying can be reduced, and a water-absorbing resin having an excellent water absorption speed can be obtained.

Examples of the additive added to the hydrogel include a drying aid.

Specifically, from the viewpoint of industrial efficiency, it is preferable to add a drying aid to the hydrogel when a particulate hydrogel having a diameter of 1 mm or less is handled. Particularly, by adding a drying aid to the hydrogel before the drying step in accordance with an embodiment of the present invention, a water-absorbing resin having an excellent water absorption speed is obtained. That is, a method for producing a water-absorbing resin in accordance with a preferred embodiment of the present invention has a step of adding a drying aid to a hydrogel polymer.

"Drying Aid"

The drying aid is added for the purpose of maintaining the fluidity of the hydrogel during stirring drying, and the drying aid is exemplified by a surfactant and/or a polymer lubricant. A polymer lubricant and a surfactant may be used in combination as the drying aid.

The amount of drying aid added is set as appropriate according to the moisture content of the drying aid and/or the type of gel fluidizing agent. The total amount of drying aid added is preferably 0.001 mass % to 0.5 mass %, more preferably 0.01 mass % to 0.3 mass %, and even more preferably 0.02 mass % to 0.2 mass %, relative to the solid content (100 mass %) of the hydrogel. Further, in a preferred embodiment of the present invention, the hydrogel polymer in the drying step contains a drying aid that accounts for less than 0.08 mass % of the solid content (100 mass %) of the hydrogel polymer. By drying the hydrogel obtained by reversed phase suspension polymerization with use of a rotary dryer as in an embodiment of the present invention, the hydrogel is less likely to fuse, and the particle diameter can be easily adjusted by crushing or the like. Therefore, in a case where the hydrogel is dried with use of a rotary dryer, the amount of drying aid used can be reduced.

The addition of the drying aid to the hydrogel polymer is preferably carried out in a step previous to the drying step. Specifically, examples of the addition of the drying aid to the hydrogel polymer include: (1) addition to a hydrogel separated from a hydrophobic organic solvent in the separation step; (2) addition to a sized gel before the drying step; (3) addition to an aqueous monomer solution in the aqueous monomer solution preparation step; (4) addition to a hydrophobic organic solvent in the dispersion step; and the like. More preferably, the addition of the drying aid to the hydrogel polymer is preferably addition carried out in the step immediately before the drying step, and is more preferably addition carried out in a period between after a step (for example, the gel sizing step) previous to the drying step and before the drying step. Furthermore, it is also a preferable embodiment to, after the drying aid has been added to the hydrogel polymer in a step (for example, the gel sizing step) previous to the drying step, further add the drying aid to the hydrogel polymer in a period between after the step (for example, the gel sizing step) previous to the drying step and before the drying step. In addition, examples of a form of the addition of the drying aid before the drying step include: a form in which the hydrogel polymer and the drying aid are charged into a dryer; a form in which the drying aid is added to the hydrogel polymer before the hydrogel polymer is charged into the dryer; and the like. Also, the drying aid may overlap with a surfactant and/or a polymer additive which is/are used as the dispersion aid in the dispersing step.

Specific examples of the surfactant used as the drying aid encompass: (1) nonionic surfactants including sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hardened castor oil, alkylallylformaldehyde-condensed polyoxyethylene ethers, polyoxyethylene polyoxypropylene block copolymers, polyoxyethylene polyoxypropyl alkyl ethers, polyethylene glycol fatty acid esters, alkyl glucosides, N-alkyl gluconamides, polyoxyethylene fatty acid amides, polyoxyethylene alkylamines, phosphates of polyoxyethylene alkyl ethers, and phosphates of polyoxyethylene alkyl aryl ethers; (2) amphoteric surfactants including: alkyl dialkylamino acetic acid betaines such as caprylic dimethylamino acetic acid betaine, lauryl dimethylamino acetic acid betaine, myristyl dimethylamino acetic acid betaine, and stearyl dimethylamino acetic acid betaine; alkylamide propyl betaines such as lauric acid amide propyl betaine, coconut oil fatty acid amide propyl betaine, and palm kernel oil fatty acid amide propyl betaine; alkyl hydroxy sulfobetaines such as lauryl hydroxy sulfobetaine; and alkyl carboxymethyl hydroxyethyl imidazolinium betaines such as 2-alkyl-N-carboxymethyl-N-hydroxyethyl imidazolinium betaine; (3) anionic including alkyl amino monoalkali metal diacetates such as lauryl amino monosodium diacetate, lauryl amino potassium diacetate, and myristyl amino sodium diacetate; (4) cationic surfactants including long-chain alkyl dimethylaminoethyl quaternary salts; and the like. One of these surfactants may be used solely, or two or more thereof may be used in combination.

Specific examples of the polymer lubricant encompass maleic anhydride-modified polyethylene, maleic anhydride-modified polypropylene, maleic anhydride-modified ethylene-propylene copolymer, maleic anhydride-modified ethylene-propylene-diene terpolymer (EPDM), maleic anhydride-modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylic acid copolymer, ethyl cellulose, hydroxyethyl cellulose, polyalkylene oxide such as polyethylene glycol, and the like. The molecular weight (weight-average molecular weight) of these polymer lubricants is selected as appropriate in the range of preferably 200 to 2,000,000 and more preferably 400 to 1,000,000. One of these polymer lubricants may be used solely, or two or more thereof may be used in combination.

"Particle Size Distribution of Dried Polymer"

As a particle size distribution of the dried polymer obtained in the drying step, the proportion of particles having a particle diameter of 850 μm or more (the proportion of particles that have not passed through a sieve with a mesh size particle diameter of 850 μm) is preferably as low as possible, and is preferably 50 mass % or less, more preferably 45 mass % or less, and even more preferably 40 mass % or less in 100 mass % of the dried polymer. According to the method in an embodiment of the present invention, the formation of coarse particles is significantly prevented by combination with drying with use of a stirring-type dryer. This makes it possible to set the proportion of the particles having a particle diameter of 850 μm or more to be in the above-described preferable range. Further, the proportion of particles having a particle diameter of 1400 μm or more in 100 mass % of the dried polymer (the proportion of particles that have not passed through a sieve with a mesh size particle diameter of 1400 μm) is preferably as small as possible, and is preferably 40 mass % or less, more preferably 35 mass % or less, and even more preferably 30 mass % or less.

<3-7> Surface-Crosslinking Step

The water-absorbing resin (for example, water-absorbing resin powder) obtained through the drying step (and the subsequent optional step) is preferably surface-crosslinked with a surface-crosslinking agent. This surface crosslinking is a process of providing a portion having a high crosslinking density on a surface layer (a portion within several tens of micrometers from the surface of water-absorbing resin (for example, water-absorbing resin powder)) of the water-absorbing resin (for example, water-absorbing resin powder). Various water absorption physical properties of a water-absorbing resin can be improved by carrying out surface-crosslinking treatment. Here, adjusting the crosslinking density of the water-absorbing resin as appropriate makes it possible to obtain excellent absorption capacity under pressure in particular.

Note that, in an embodiment of the present invention, known surface crosslinking techniques are employed as appropriate, including surface crosslinking in a state dispersed in a hydrophobic organic solvent, which is carried out in the conventional reversed phase suspension polymerization, and surface crosslinking to powder in a dry state, which is generally carried out in aqueous solution polymerization. In an embodiment of the present invention, surface crosslinking to a water-absorbing resin that has undergone the gel separation step and the drying step is preferable from the viewpoint of improvement in absorption capacity under pressure. Note that the surface-crosslinking agent used in the surface-crosslinking step is also presented as a "postcrosslinking agent" in the known technique in order to be distinguished from the internal crosslinking agent used in the aqueous monomer solution preparation step.

In an embodiment of the present invention, the surface-crosslinking step may be carried out after the above-described drying step or during the drying step. In a known surface-crosslinking step, a surface-crosslinking agent is generally mixed with a hydrogel polymer (for example, a hydrogel crosslinked polymer) or a dried polymer (for example, a crosslinked polymer) which is a dried product of the hydrogel polymer, and the mixture is heated to carry out a crosslinking reaction. In an embodiment of the present invention, these steps may be separately provided after the above-described drying step, or a surface-crosslinking agent may be added to the hydrogel polymer in the drying step to simultaneously carry out surface-crosslinking reaction of the polymer and drying thereof. Further, in a case where a water-absorbing resin is produced by a batch-type reversed phase suspension polymerization method, the hydrophobic organic solvent and the hydrogel polymer can be separated by carrying out distillation in the separation step after the polymerization reaction. In the batch-type reversed phase suspension polymerization method, adding a surface-crosslinking agent to the hydrogel polymer in the middle of the separation step also makes it possible to obtain a crosslinked water-absorbing resin (for example, water-absorbing resin particles).

<3-8> Other Steps

A method for producing a water-absorbing resin in accordance with an embodiment of the present invention can include, in addition to the above-described steps, optionally a cooling step, a pulverizing step, a hydration (re-moistening) step, an other additive addition step, a classification step, a sizing step, and a fine powder reuse step. Further, the method for producing a water-absorbing resin in accordance with an embodiment of the present invention may further include a conveying step, a storing step, a packing step, a reserving step, and the like.

(Cooling Step)

In the cooling step carried out optionally, the particulate dried polymer obtained in the drying step is cooled with use of a known cooling means, so that a particulate dried polymer cooled to a desired temperature can be obtained.

(Pulverizing Step)

A method for producing a water-absorbing resin in accordance with an embodiment of the present invention preferably includes the pulverizing step of pulverizing a particulate dried polymer obtained in the drying step (and the subsequent optional cooling step). Carrying out the pulverization step makes it possible to obtain a water-absorbing resin (for example, water-absorbing resin powder) having a controlled particle diameter or a controlled particle size distribution.

In the pulverizing step, for example, a high-speed rotation pulverizer such as a roll mill, a hammer mill, a screw mill, or a pin mill; a vibration mill; a knuckle-type pulverizer; a cylindrical mixer; or the like is selected as appropriate and used as a pulverizing means.

(Re-Moistening Step)

The re-moistening step carried out optionally is step of adding, to the water-absorbing resin (for example, water-absorbing resin particles) obtained in the surface-crosslinking step, at least one additive selected from the group consisting of a polyvalent metal salt, a cationic polymer, a chelating agent, an inorganic reducing agent, and α-hydroxycarboxylic acid compound. The polyvalent metal salt is preferably a water-soluble polyvalent metal salt and more preferably a water-soluble aluminum salt. Examples of the water-soluble aluminum salt encompass aluminum sulfate.

In the re-moistening step, the above-described additive in the form of an aqueous solution or a dispersion (slurry) is preferably added to a water-absorbing resin (for example, water-absorbing resin particles). Note that the additive may be added, to the water-absorbing resin, together with the above-mentioned surface-crosslinking agent solution, and mixed with the water-absorbing resin. Specifically, the re-moistening step is exemplified by a method described in "(2-7) Re-moistening step" of International Patent Publication No. WO 2015/053372, and such a method can also be employed in an embodiment of the present invention.

(Other Additive Addition Step)

In an embodiment of the present invention, an additive other than the above-described additives can be added in order to give various functions to the water-absorbing resin. Specifically, examples of such an additive encompass a surfactant, a compound having a phosphorus atom, an oxidizer, an organic reducing agent, water-insoluble inorganic fine particles, organic powder such as metallic soap, a deodorizing agent, an antibacterial agent, pulp, thermoplastic fibers, and the like. Note that the water-insoluble inorganic fine particles are exemplified by a compound disclosed in "<5> Water-insoluble inorganic fine particles" of International Publication No. WO 2011/040530, and such a compound can be employed in an embodiment of the present invention. Among these additives, one or more selected from the group consisting of a polyvalent metal salt, a cationic polymer, and inorganic fine particles, which preferably improve the liquid permeability so that the water-absorbing resin does not impair the water absorption physical properties especially when the swollen gel layer is compressed, is preferably added to the water-absorbing resin. The polyvalent metal salt is preferably a water-soluble polyvalent metal salt and more preferably a water-soluble aluminum salt. Examples of the water-soluble aluminum salt encompass aluminum sulfate.

(Sizing Step)

The "sizing step" means a step of adjusting the particle diameter by disintegrating a water-absorbing resin (for example, water-absorbing resin powder) having been loosely aggregated through the surface-crosslinking step. Note that this sizing step encompasses a fine powder removal step and a classification step, which are steps subsequent to the surface-crosslinking step. In an embodiment of the present invention, the sizing step is preferably carried out from the viewpoint of adjusting the particle diameter of a water-absorbing resin and obtaining stable water absorption physical properties.

(Fine Powder Reuse Step)

The "fine powder reuse step" means a step of supplying, to any of the steps, the hydrogel or the fine powder of the water-absorbing resin generated by, for example, sieve classification in each of the above steps as it is or after having granulated the fine powder. In an embodiment of the present invention, the fine powder reuse step is preferably carried out from the viewpoint of the fine powder reuse step reducing a production loss of a water-absorbing resin.

<4> Application of Water-Absorbing Resin

A water-absorbing resin and an absorbent body in accordance with an embodiment of the present invention enable provision of an absorbent article that prevents swelling of a water-absorbing portion when used in a thin absorbent article. More specifically, a water-absorbing resin and an absorbent body in accordance with an embodiment of the present invention are such that a gel layer of an absorbent core is compressed by repeated application of a load (weight) when used in a thin absorbent article, and thus make it possible to provide an absorbent article that prevents swelling of a core even when used for a long period of time. An application of the water-absorbing resin in accordance with an embodiment of the present invention is not particularly limited. A preferable application thereof is exemplified by an absorbent body in an absorbent article such as disposable diapers (for infants and for adults), sanitary napkins, and incontinence pads. The water-absorbing resin in accordance with an embodiment of the present invention can be suitably used as an absorbent body for thin high-concentration disposable diapers in which swelling of an absorbent core due to a swollen gel after liquid absorption has been a problem. Examples of other absorbent article encompass: soil water retention agents; raising sheets; seed coating materials; dew condensation prevention sheets; drip absorbers; freshness-keeping materials; disposable body warmers; cooling bandanas; ice packs; medical waste liquid solidifying agents; surplus soil solidifying agents; water loss prevention waste liquid gelatinizers; absorption sandbags; portable toilets for disaster; fomentation materials; thickeners for cosmetics; waterproof materials for electric and electronic material communication cables; gasket packings; sustained-release agents for fertilizer; various sustained-release agents (such as space disinfectants and air fresheners); pet sheets; cat sands; dressing materials for wound protection; building materials for dew condensation prevention; moisture-in-oil removers; additives for resins such as paints, adhesives, anti-blocking agents, light diffusing agents, matting agents, additives for decorative boards, additives for artificial marble, and additives for toner; and the like.

Further, as a material for the absorbent body, an absorbent material such as pulp fibers can be used together with the water-absorbing resin. In such a case, the content (core concentration) of the water-absorbing resin in 100 mass % of the absorbent body is preferably 30 mass % to 100 mass %, more preferably 40 mass % to 100 mass %, even more preferably 50 mass % to 100 mass %, further more preferably 60 mass % to 100 mass %, particularly preferably 70 mass % to 100 mass %, and most preferably 75 mass % to 95 mass %.

In a case where the absorbent body having the core concentration in the above range is used as an upper layer part of an absorbent article, the absorbent article can maintain cleanness, i.e., a state of being white. Further, the absorbent body having the core concentration in the above range is excellent in diffusion property with respect to a body fluid or the like such as urine and/or blood and thus achieves efficient liquid distribution. Therefore, improvement in absorption amount can be expected.

More specifically, the above-described absorbent body may be an absorbent body which contains a water-absorbing resin in accordance with an embodiment of the present invention and which does not contain hydrophilic fibers. Alternatively, the above-described absorbent body may be an absorbent body which contains a water-absorbing resin in accordance with an embodiment of the present invention and hydrophilic fibers and in which the mass of the water-absorbing resin accounts for 50 mass % or more of 100 mass % in total of the water-absorbing resin and the hydrophilic fibers.

In a case where an absorbent body contains the water-absorbing resin in accordance with an embodiment of the present invention and hydrophilic fibers, the mass of the water-absorbing resin accounts for preferably 50 mass % or more and less than 100 mass %, more preferably 60 mass % or more and less than 100 mass %, more preferably 70 mass % or more and less than 100 mass %, more preferably 80 mass % or more and less than 100 mass %, even more preferably 90 mass % or more and less than 100 mass %, particularly preferably 90 mass % to 95 mass % of 100 mass % in total of the water-absorbing resin and the hydrophilic fibers. The absorbent body containing the water-absorbing resin having a mass in the above-described range has the following advantage(s): (1) the advantage that, in a case where the absorbent body is used as an upper layer part of an absorbent article, the absorbent article can maintain cleanness, i.e., a state of being white; and/or (2) the advantage that, since the absorbent body is excellent in diffusion property with respect to a body fluid or the like such as urine and/or blood, the absorbent body achieves efficient liquid distribution, and thus improvement in absorption amount can be expected.

The hydrophilic fibers are not particularly limited, and examples of the hydrophilic fibers encompass pulp fibers, cotton linter crosslinked cellulose fibers, rayon, cotton, wool, acetate, vinylon, and the like.

An embodiment of the present invention can also be configured as follows.

<1> A water-absorbing resin, wherein said water-absorbing resin is a poly(meth)acrylic acid (salt)-based water-absorbing resin and has a swollen gel compressibility rate of 3% or more expressed by the following (Formula 1):

$$\text{Swollen gel compressibility rate [\%]} = (D1 - D2)/D1 \times 100, \quad \text{(Formula 1)}$$

where D1 is a thickness [mm] of a swollen gel layer formed by the water-absorbing resin when a measurement device which is equipped with a piston having a diameter of 59 mm and a cell having a bottom portion in a mesh form and having an inner diameter of 60 mm and in which 1.0 g of the water-absorbing resin is spread on the bottom portion has been placed in a petri dish containing a 0.9 mass % aqueous sodium chloride solution to allow the water-absorbing resin to absorb the 0.9 mass % aqueous sodium chloride solution for 5 minutes, and D2 is a thickness [mm] of the swollen gel layer formed by the water-absorbing resin after an operation of setting the measurement device on a sieve having a mesh size of 4750 μm, placing a weight on the piston so that a load of 0.7 psi is applied to the swollen gel layer, allowing the cell to stand still for 10 seconds, and then removing the weight has been repeated ten times.

<2> The water-absorbing resin according to <1>, which is an aggregate-like particle of spherical particles.

<3> The water-absorbing resin according to <1> or <2>, which has a mass average particle diameter (D50) of 50 μm to 700 μm.

<4> The water-absorbing resin according to any one of <1> to <3>, wherein the thickness D2 is less than 15 mm.

<5> The water-absorbing resin according to any one of <1> to <4>, wherein the thickness D1 is less than 15 mm.

<6> The water-absorbing resin according to any one of <1> to <5>, which has a water absorption capacity under pressure (AAP) of 18 g/g or more.

<7> The water-absorbing resin according to any one of <1> to <6>, which is obtained by carrying out reversed phase suspension polymerization in a hydrophobic organic solvent.

<8> The water-absorbing resin according to any one of <1> to <7>, which is obtained by extruding spherical particles using an extruder having a porous plate.

<9> An absorbent body, wherein said absorbent body contains a water-absorbing resin according to any one of <1> to <8>, and (1) does not contain hydrophilic fibers or (2) contains hydrophilic fibers and is such that a mass of the water-absorbing resin accounts for 50 mass % or more of 100 mass % in total of the water-absorbing resin and the hydrophilic fibers.

EXAMPLES

The following description will discuss an embodiment of the present invention more concretely with reference to Examples and Comparative Example shown below. Note, however, that the present invention is not limited to these Examples and Comparative Example, and that any Example derived from a proper combination of technical means described in respective different Examples is also encompassed in the technical scope of the present invention. Note that, although "part(s)" and "%" may be used in Examples, "part(s)" and "%" indicate "part(s) by mass" and "mass %", respectively, unless otherwise noted. In addition, the operations are carried out at room temperature (for example, 25° C.) unless otherwise specified. Note that electric devices/apparatuses (including devices/apparatuses used to measure physical properties of water-absorbing resins) used in Examples and Comparative Example each used a 200-V or 100-V electric power supply with a frequency of 60 Hz, unless otherwise specified.

<Evaluation Method>

[Number Average Particle Diameter]

A scanning electron microscope photograph (SEM) of a water-absorbing resin or water-absorbing resin powder was taken. From the photograph, 50 primary particles on the front of the aggregate-like particle (secondary particle) were randomly selected. The major axis and minor axis of each primary particle were measured, and a value obtained by averaging products of the measured values (a geometric mean value of the measured values) was assumed to be a primary particle diameter. The primary particle diameters of the 50 primary particles were calculated, and an average value of the values thus obtained was assumed to be an average primary particle diameter of the water-absorbing resin.

[Moisture Content]

The moisture content was measured in conformity with an EDANA method (ERT 430.2-02). Note that, at the time of the measurement, the mass of a sample (water-absorbing resin or water-absorbing resin powder) was changed to 1.0 g, the drying temperature was changed to 180° C., and the drying time was changed to 3 hours. Specifically, 1.0 g of the sample (water-absorbing resin or water-absorbing resin powder) was put into an aluminum cup having a 50-mm-diameter bottom surface, and then a total mass W1 (g) of the aluminum cup (the aluminum cup containing the water-absorbing resin or the water-absorbing resin powder) was weighed accurately. Next, the aluminum cup (the aluminum cup containing the water-absorbing resin or the water-absorbing resin powder) was allowed to stand still in an oven set to an atmospheric temperature of 180° C. After a lapse of 3 hours, the aluminum cup (the aluminum cup containing the water-absorbing resin or the water-absorbing resin powder) was taken out from the oven, and a total mass W2 (g) was weighed accurately. When the mass of the sample (the water-absorbing resin or the water-absorbing resin powder) used in this measurement was assumed to be M (1.0 g), the moisture content (mass %) of the sample was determined in accordance with the following (Formula 2):

$$\text{Moisture content (mass\%)} = \{(W1 - W2)/M\} \times 100. \quad \text{Formula (2)}$$

[Mass Average Particle Diameter (D50)]

The mass average particle diameter (D50) was measured in accordance with a method described in "(3) Mass-Average Particle Diameter (D50) and Logarithmic Standard Deviation ($\sigma\zeta$) of Particle Diameter Distribution" described in Columns 27 and 28 of U.S. Pat. No. 7,638,570. Specifically, 10.0 g of a water-absorbing resin was placed, at a room temperature (20° C. to 25° C.) and a humidity of 50 RH %, in JIS standard sieves (THE IIDA TESTING SIEVE, diameter: 8 cm) having respective mesh sizes of 850 μm, 710 μm, 600 μm, 500 μm, 425 μm, 300 μm, 212 μm, 150 μm, and 45 μm, and a vibration classifier (IIDA SIEVE SHAKER, Type: ES-65, Ser. No. 0501) was used to carry out classification for 5 minutes. After that, a residual percentage R on each of the sieves was plotted on a logarithmic probability paper. Thus, a particle size corresponding to R=50 mass % was read as the mass average particle diameter (D50).

[CRC]

The centrifuge retention capacity (CRC) was measured in conformity with an EDANA method (ERT 441.2-02). Specifically, a water absorption capacity (unit: g/g) was determined after 0.2 g of water-absorbing resin was contained in a nonwoven fabric bag, the nonwoven fabric bag was immersed in a large excess of a 0.9 mass % aqueous sodium chloride solution for 30 minutes to allow the water-absorbing resin to freely swell, and then the water-absorbing resin was drained for 3 minutes with use of a centrifuge (250 G).

[AAP]

The AAP (absorption capacity under pressure) was measured in conformity with an EDANA method (ERT 442.2-02). Note that the load condition was changed to 4.83 kPa (0.7 psi).

[Ext]

The Ext (water-soluble component) of the water-absorbing resins in Examples of the present invention and Comparative Example was measured in conformity with an EDANA method (ERT 470.2-02).

[Bulk Density]

The bulk density of a water-absorbing resin was measured in conformity with an EDANA method (T460.2-02).

[Swollen Gel Compressibility Rate]

The swollen gel compressibility rate of a water-absorbing resin was measured by the procedure presented below. The measurement device used for the measurement of the swollen gel compressibility rate will be described with reference to FIGS. 1 and 2.

1.0 g of a water-absorbing resin 16 was evenly spread on a bottom portion 15 of a cell 11 having an internal diameter of 60 mm, the bottom portion 15 being formed of a stainless steel mesh (mesh size of 36 μm=400 mesh). Next, a piston 12 having a diameter of 59 mm and a weight of 108 g was mounted in the cell 11 from above the water-absorbing resin 16. After that, the cell 11 was placed in a petri dish 13 of 19.8 cm×19.8 cm containing 180 g of a 0.9 mass % (mass/mass %) aqueous sodium chloride solution of 25° C., and the water-absorbing resin 16 was allowed to absorb the 0.9 mass % aqueous sodium chloride solution for 5 minutes. By this operation, the water-absorbing resin 16 was swollen to form a swollen gel layer. After that, the thickness (D1 [mm]) of the swollen gel layer formed by the swollen water-absorbing resin 16 was measured. Subsequently, an operation of setting the cell 11 on a JIS standard sieve having a mesh size of 4750 μm with the piston 12 mounted, placing a weight 14 of 1283 g on the piston 12 so that a load of 0.7 psi was applied to the swollen gel, allowing the cell 11 to stand still for 10 seconds, and then removing the weight 14 was repeated ten times. Note that, immediately after the weight 14 had been removed, a load was applied for next 10 seconds. After that, the thickness (D2 [mm]) of the swollen gel layer formed by the swollen water-absorbing resin 16 was measured, and the swollen gel compressibility rate was calculated based on the following (Formula 1):

$$\text{Swollen gel compressibility rate [\%]} = (D1 - D2)/D1 \times 100. \quad \text{(Formula 1)}$$

Note that, in Table 2, D1 denotes "thickness of swollen gel before compression", and D2 denotes "thickness of swollen gel after compression".

[Thickness Compressibility Rate of Absorbent Sheet (Absorbent Body)]

(1) Preparation of Absorbent Sheet (Absorbent Body)

Figure 3:
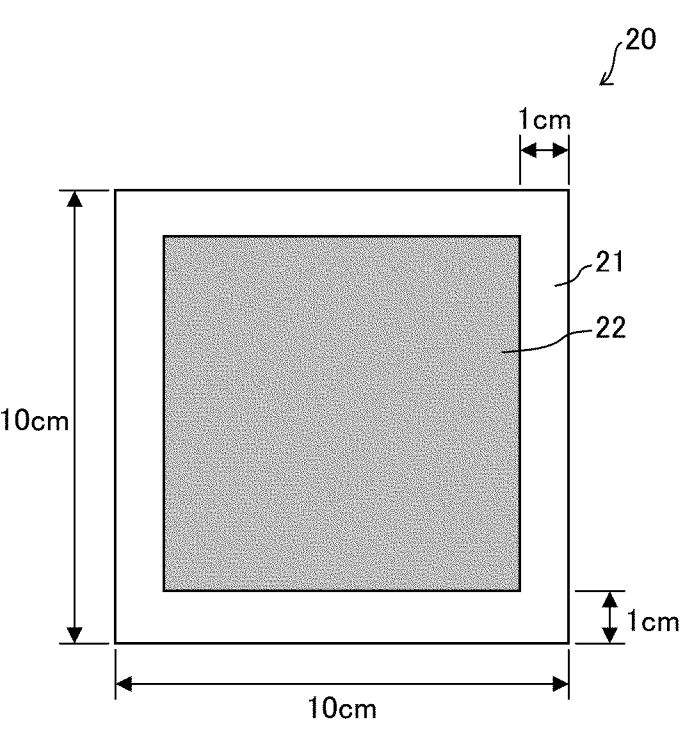
FIG. 3 is a plan view illustrating an absorbent sheet for evaluation prepared in Examples in a process of preparing the absorbent sheet for evaluation.
Figure 4:
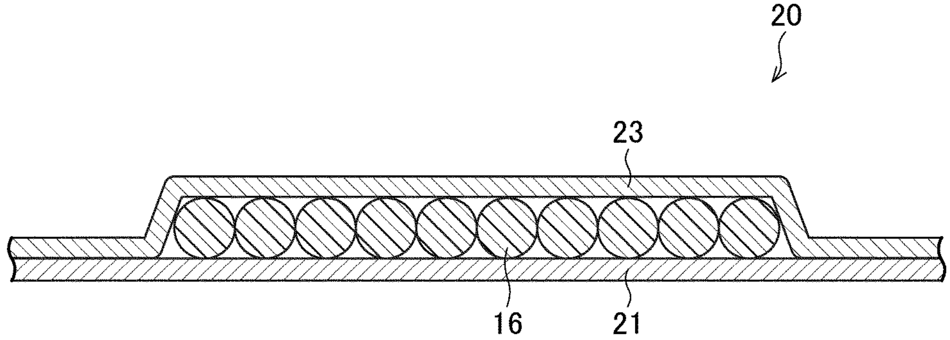
FIG. 4 is a cross-sectional view illustrating the absorbent sheet for evaluation prepared in Examples.

A method for preparing an absorbent sheet (absorbent body) 20 used to measure a thickness compressibility rate of an absorbent sheet (absorbent body) will be described with reference to FIGS. 3 and 4. FIG. 3 is a plan view illustrating an absorbent sheet 20 for evaluation prepared in Examples in a process of preparing the absorbent sheet 20 for evaluation. FIG. 3 illustrates an area in which the water-absorbing resin 16 is spread (that is, a water-absorbing resin spread area 22) on an adhesive surface of an adhesive tape 21. FIG. 4 is a cross-sectional view illustrating the absorbent sheet 20 for evaluation prepared in Examples. FIG. 4 illustrates an inner configuration of the obtained absorbent sheet 20 for evaluation. FIGS. 3 and 4 are also described as drawings illustrating a method for producing an absorbent body in accordance with an embodiment of the present invention.

First, as illustrated in FIG. 3, on the adhesive surface of the adhesive tape 21 (vinyl tape No. 21S available from NITTO DENKO) cut to 10 cm×10 cm, 1.0 g of the water-absorbing resin 16 was evenly spread over an area 1 cm inward of an edge on each of the four sides of the adhesive tape 21 (that is, an 8 cm×8 cm area (water-absorbing resin spread area 22) in the center of the adhesive tape). Further, from above the water-absorbing resin 16, a 10 cm×10 cm nonwoven fabric 23 (air-laid nonwoven fabric having a basis weight of 46.6 g/$m^2$) was placed, and the nonwoven fabric 23 and the adhesive surfaces of the four sides of the adhesive tape 21 were bonded together to prepare the absorbent sheet 20 for evaluation having a laminated structure (a structure in which the adhesive tape 21, the water-absorbing resin 16, and the nonwoven fabric 23 are stacked in this order) illustrated in FIG. 4. The absorbent sheet 20 for evaluation is also described as an absorbent body containing the water-absorbing resin 16 and containing no hydrophilic fibers.

(2) Measurement of Thickness Compressibility Rate of Absorbent Sheet (Absorbent Body) 20

On a flat table, the absorbent sheet 20 (absorbent body) for evaluation was placed on an acrylic plate (10 cm×23 cm, thickness of 0.3 cm), 25 mL of a 0.9 mass % aqueous sodium chloride solution of 20° C. was added to the absorbent sheet 20 for evaluation over 2 minutes to allow the water-absorbing resin 16 in the absorbent sheet 20 for evaluation to swell. Three minutes after the end of the addition of the 0.9 mass % aqueous sodium chloride solution, the thickness (D1' [mm]) of the absorbent sheet 20 for evaluation was measured. Subsequently, another acrylic plate (10 cm×23 cm, thickness of 0.3 cm) was placed on the absorbent sheet 20 for evaluation. Furthermore, an operation of placing a weight of 1.0 kg on the acrylic plate, allowing the absorbent sheet 20 for evaluation to stand still for 10 seconds, and removing the weight was repeated ten times. Note that, immediately after the weight had been removed, a load was applied for next 10 seconds. After that, the acrylic plate on the absorbent sheet 20 for evaluation was removed, the thickness (D2' [mm]) of the absorbent sheet 20 for evaluation was measured, and the thickness compressibility rate of the absorbent sheet 20 (absorbent body) for evaluation was calculated based on the following (Formula 3):

$$\text{Thickness compressibility rate } [\%]=(D1'-D2')/D1'\times 100 \quad \text{(Formula 3)}.$$

Note that, in Table 3, D1' denotes "thickness of absorbent sheet before compression", and D2' denotes "thickness of absorbent sheet after compression".

Example 1

800 g of n-heptane was placed in a 2000-ml four-necked separable flask equipped with a stirrer, a reflux condenser, a thermometer, a nitrogen gas introduction tube, and a dropping funnel, and 0.88 g of maleic anhydride-modified ethylene-propylene copolymer (Hi-WAX (registered trademark) HW2203A, available from Mitsui Chemicals Co., Ltd.) as a dispersion aid was added, and the maleic anhydride-modified ethylene-propylene copolymer was dissolved in n-heptane to obtain a heptane solution. Next, nitrogen gas was blown into the obtained heptane solution to expel dissolved oxygen in the heptane solution.

Separately prepared in a flask was an aqueous monomer solution (1) composed of 127 g of sodium acrylate, 36 g of acrylic acid, 0.097 g of polyethylene glycol diacrylate (n=9), 0.008 g of pentasodium diethylenetriamine pentaacetate, 0.67 g of hydroxyethyl cellulose as a thickener, and 215 g of ion-exchanged water, and nitrogen gas was blown into the aqueous monomer solution (1) to expel dissolved oxygen dissolved in the aqueous monomer solution (1). Next, after 1.2 g of a 15% (mass/mass %) aqueous solution of sodium persulfate had been added to the aqueous monomer solution (1) in this flask, the whole amount of a resulting solution was added to the separable flask. By stirring the mixture solution in the separable flask at 210 rpm, the aqueous monomer solution (1) was dispersed in the heptane solution. After that, the temperature of a bath in which the separable flask was immersed was increased to 60° C. to initiate a polymerization reaction. After this bath temperature of 60° C. was maintained for 2 hours, the polymerization was stopped, and filtration was carried out by suction filtration, and a residue was air-dried overnight to obtain a hydrogel polymer (1). The average primary particle diameter of the hydrogel polymer (1) was 180 μm.

Next, the hydrogel polymer (1) (gel temperature: 90° C.) was charged into a gel sizing apparatus having a screw and a porous plate having a hole diameter of 0.8 mm, and the hydrogel polymer (1) was discharged from the gel sizing apparatus to obtain a sized gel (1).

Subsequently, the sized gel (1) was dried with use of a cylindrical container rotary dryer. Specifically, in an atmosphere at a temperature of 200° C., the rotary container provided in the cylindrical container rotary dryer was rotated at 75 rpm, the sized gel (1) after heating was supplied to the cylindrical container rotary dryer, and drying was carried out to obtain a dried polymer (1). The moisture content of the dried polymer (1) was 10 mass %.

Subsequently, the dried polymer (1) was supplied to a roll mill (pulverizer) and pulverized to adjust the particle size, and further classified with use of a sieve having a mesh size particle diameter of 150 μm to obtain water-absorbing resin powder (1). The mass average particle diameter of the water-absorbing resin powder (1) was 380 μm.

To 100 parts by mass of the water-absorbing resin powder (1), a surface-crosslinking agent solution composed of 0.03 parts by mass of ethylene glycol diglycidyl ether, 0.385 parts by mass of ethylene carbonate, 0.644 parts by mass of propylene glycol, and 2.6 parts by mass of ion-exchanged water was sprayed with a spray, followed by uniform mixing with use of a high speed continuous mixer.

A resulting mixture was introduced into a heat treatment machine adjusted to an atmospheric temperature of 195° C.±2° C. and heat-treated for 30 minutes. Then, the powder temperature was forcibly cooled to 60° C. to obtain surface-crosslinked water-absorbing resin powder (1).

To 100 parts by mass of the surface-crosslinked water-absorbing resin powder (1), a surface-crosslinking agent solution composed of 1.17 parts by mass of a 27.5 mass % aqueous aluminum sulfate solution (8 mass % in terms of aluminum oxide), 0.196 parts by mass of a 60 mass % aqueous sodium lactate solution, and 0.029 parts by mass of propylene glycol was mixed uniformly. Further, to 100 parts by mass of the water-absorbing resin powder (1) after mixing, 10.0 mass % water was mixed uniformly.

After that, a resulting mixture was crushed (sized) until the mixture passed through a JIS standard sieve having a mesh size of 710 μm, so that a water-absorbing resin (1) was obtained. The obtained water-absorbing resin (1) was particulate. More specifically, the obtained water-absorbing resin (1) was an aggregate-like particle of spherical particles. Tables 1 to 3 show physical properties of the obtained water-absorbing resin (1).

Example 2

800 g of cyclohexane was placed in a 2000-ml four-necked separable flask equipped with a stirrer, a reflux condenser, a thermometer, a nitrogen gas introduction tube, and a dropping funnel, 0.6 g of sucrose fatty acid ester (DK Ester (registered trademark) F-50, available from DKS Co., Ltd., HLB=6) as a dispersion aid was added, and the sucrose fatty acid ester was dissolved in cyclohexane to obtain a cyclohexane solution. Next, nitrogen gas was blown into the obtained cyclohexane solution to expel dissolved oxygen in the cyclohexane solution.

Separately prepared in a flask was an aqueous monomer solution (2) composed of 141 g of sodium acrylate, 36 g of acrylic acid, 0.022 g of N,N'-methylenebisacrylamide, 0.71 g of hydroxyethyl cellulose as a thickener, and 327.65 g of ion-exchanged water, and nitrogen gas was blown into the aqueous monomer solution (2) to expel dissolved oxygen dissolved in the aqueous monomer solution (2). Next, after 0.95 g of a 15% aqueous solution of sodium persulfate had been added to the aqueous monomer solution (2) in this flask, the whole amount of a resulting solution was added to the separable flask. By stirring the mixture solution in the separable flask at 370 rpm, the aqueous monomer solution (2) was dispersed in the cyclohexane solution. After that, the temperature of a bath in which the separable flask was immersed was increased to 60° C. to initiate a polymerization reaction. After this bath temperature of 60° C. was maintained for 2 hours, the polymerization was stopped, and filtration was carried out by suction filtration, and a residue was air-dried overnight to obtain a hydrogel polymer (2). The average primary particle diameter of the hydrogel polymer (2) was 195 μm.

Next, the hydrogel polymer (2) (gel temperature: 90° C.) was charged into a gel sizing apparatus having a screw and a porous plate having a hole diameter of 0.8 mm, and the hydrogel polymer (2) was discharged from the gel sizing apparatus to obtain a sized gel (2).

Next, 3.2 kg of the sized gel (2) obtained above was put into a heat retention chamber. As a result of allowing the sized gel (2) to stand still in the heat retention chamber, the temperature of the sized gel (2) at the time of supply to the dryer reached 80° C.

Subsequently, the sized gel (2) was dried with use of a cylindrical container rotary dryer. Specifically, in an atmosphere at a temperature of 200° C., the rotary container provided in the cylindrical container rotary dryer was rotated at 75 rpm, the sized gel (2) after heating was supplied to the cylindrical container rotary dryer, and drying was carried out to obtain a dried polymer (2). The moisture content of the dried polymer (2) was 8 mass %.

Subsequently, the dried polymer (2) was supplied to a roll mill (pulverizer) and pulverized to adjust the particle size, and further classified with use of a sieve having a mesh size particle diameter of 150 μm to obtain water-absorbing resin powder (2). The mass average particle diameter of the water-absorbing resin powder (2) was 110 μm.

Subsequently, to 100 parts by mass of the water-absorbing resin powder (2), a surface-crosslinking agent solution composed of 0.1 parts by mass of ethylene glycol diglycidyl ether, 1.0 part by mass of isopropyl alcohol, and 3.0 parts by mass of ion-exchanged water was sprayed with a spray, followed by uniform mixing with use of a high speed continuous mixer.

A resulting mixture was introduced into a heat treatment machine adjusted to an atmospheric temperature of 100° C. and heat-treated for 40 minutes. Then, the powder temperature was forcibly cooled to 60° C. to obtain surface-crosslinked water-absorbing resin powder (2).

To 100 parts by mass of the surface-crosslinked water-absorbing resin powder (2), a surface-crosslinking agent solution composed of 1.17 parts by mass of a 27.5 mass % aqueous aluminum sulfate solution (8 mass % in terms of aluminum oxide), 0.196 parts by mass of a 60 mass % aqueous sodium lactate solution, and 0.029 parts by mass of propylene glycol was further mixed uniformly.

After that, a resulting mixture was crushed (sized) until the mixture passed through a JIS standard sieve having a mesh size of 300 μm, so that a water-absorbing resin (2) was obtained. The obtained water-absorbing resin (2) was particulate. More specifically, the obtained water-absorbing resin (2) was spherical particles. Tables 1 to 3 show physical properties of the obtained water-absorbing resin (2).

Example 3

500 g of n-heptane was placed in a 2000-ml five-necked cylindrical round-bottomed flask equipped with a stirrer, a reflux condenser, a dropping funnel, a thermometer, and a nitrogen gas introduction tube, 0.92 g of sucrose fatty acid ester (S-370, available from Mitsubishi Chemical Corporation, HLB=3) as a dispersion aid was added and dispersed. The temperature was increased, and the sucrose fatty acid ester was dissolved in n-heptane to obtain a heptane solution. After that, the obtained heptane solution was cooled to 55° C.

Separately from this, 73.6 g of acrylic acid was placed in a 500-mL Erlenmeyer flask. While this was cooled from the outside, 102.2 g of a 30 mass % (mass/mass %) aqueous sodium hydroxide solution was added dropwise to the Erlenmeyer flask to neutralize 75 mol % of acrylic acid. Further, 0.71 g of hydroxyethyl cellulose as a thickener, 68.6 g of ion-exchanged water, 0.11 g of potassium persulfate, and 0.0092 g of ethylene glycol diglycidyl ether were added to the Erlenmeyer flask to prepare an aqueous monomer solution (3A) for first-stage polymerization.

The whole amount of this aqueous monomer solution (3A) for first-stage polymerization was added to the above-described five-necked cylindrical round-bottomed flask while being stirred by the stirrer at a rotation speed of 450 rpm, so that the aqueous monomer solution (3A) was dispersed in the heptane solution. Next, the inside of the system was sufficiently replaced with nitrogen, and then the temperature was increased. The temperature of a bath in which the round-bottomed flask was immersed was maintained at 70° C., the polymerization reaction was carried out for 1 hour, and then a resulting polymerization slurry liquid was cooled to room temperature.

95.28 g of acrylic acid was placed in another 500-mL capacity Erlenmeyer flask. While this was cooled, 132.2 g of a 30 mass % aqueous sodium hydroxide solution was added dropwise to the Erlenmeyer flask to neutralize 75 mol % of acrylic acid. Further, 51.2 g of ion-exchanged water, 0.14 g of potassium persulfate, and 0.0357 g of ethylene glycol diglycidyl ether were added to the Erlenmeyer flask to prepare an aqueous monomer solution (3B) for second-stage polymerization. The aqueous monomer solution (3B) was cooled with use of an ice water bath.

After the whole amount of this aqueous monomer solution (3B) for second-stage polymerization had been added to the polymerization slurry liquid, the inside of the system was sufficiently replaced with nitrogen again, and then the bath temperature was increased to 70° C. to initiate a polymerization reaction. After the polymerization reaction was carried out for 2 hours, the polymerization was stopped, filtration was carried out by suction filtration, and a residue was air-dried overnight to obtain a hydrogel polymer (3). The first particle diameter of the hydrogel polymer (3) was 70 μm.

Next, the hydrogel polymer (3) (gel temperature: 90° C.) was charged into a gel sizing apparatus having a screw and a porous plate having a hole diameter of 0.8 mm, and the hydrogel polymer (3) was discharged from the gel sizing apparatus to obtain a sized gel (3).

Subsequently, the sized gel (3) was dried with use of a cylindrical container rotary dryer. Specifically, in an atmosphere at a temperature of 200° C., the rotary container provided in the cylindrical container rotary dryer was rotated at 75 rpm, the sized gel (3) after heating was supplied to the cylindrical container rotary dryer, and drying was carried out to obtain a dried polymer (3). The moisture content of the dried polymer (3) was 7 mass %.

Subsequently, the dried polymer (3) was supplied to a roll mill (pulverizer) and pulverized to adjust the particle size, and further classified with use of a sieve having a mesh size particle diameter of 150 μm to obtain water-absorbing resin powder (3). The mass average particle diameter of the water-absorbing resin powder (3) was 400 μm.

Subsequently, to 100 parts by mass of the water-absorbing resin powder (3), a surface-crosslinking agent solution composed of 0.18 parts by mass of ethylene glycol diglycidyl ether, 1.5 parts by mass of propylene glycol, and 5.0 parts by mass of ion-exchanged water was sprayed with a spray, followed by uniform mixing with use of a high speed continuous mixer.

A resulting mixture was introduced into a heat treatment machine adjusted to an atmospheric temperature of 100° C. and heat-treated for 40 minutes. Then, the powder temperature was forcibly cooled to 60° C. to obtain surface-crosslinked water-absorbing resin powder (3).

To 100 parts by mass of the surface-crosslinked water-absorbing resin powder (3), a surface-crosslinking agent solution composed of 1.17 parts by mass of a 27.5 mass % (mass/mass %) aqueous aluminum sulfate solution (8 mass % in terms of aluminum oxide), 0.196 parts by mass of a 60 mass % aqueous sodium lactate solution, and 0.029 parts by mass of propylene glycol was further mixed uniformly.

After that, a resulting mixture was crushed (sized) until the mixture passed through a JIS standard sieve having a mesh size of 710 μm, so that a water-absorbing resin (3) was obtained. The obtained water-absorbing resin (3) was particulate. More specifically, the obtained water-absorbing resin (3) was an aggregate-like particle of spherical particles. Tables 1 to 3 show physical properties of the obtained water-absorbing resin (3).

Comparative Example 1

A water-absorbing resin was obtained by aqueous solution polymerization. That is, in a polypropylene container having a capacity of 1 L, 296 g of 48.5 mass % aqueous sodium hydroxide solution, 354 g of acrylic acid, 1.00 g of polyethylene glycol diacrylate (average number of ethylene oxide units: 9), 21.66 g of a 0.1 mass % aqueous pentasodium diethylenetriamine pentaacetate solution, and 319 g of ion-exchanged water were charged, and the charged raw materials were stirred to prepare a comparative aqueous monomer solution (1) composed of these raw materials.

The stirring of the comparative aqueous monomer solution (1) was continued, and the comparative aqueous monomer solution (1) was heated. At the point in time when the liquid temperature of the comparative aqueous monomer solution (1) reached 78° C., 15.8 g of a 3.8 weight % aqueous sodium persulfate solution was added to the comparative aqueous monomer solution (1). A resulting mixture solution was immediately poured into a stainless steel vat-type reaction apparatus (bottom surface: 340 mm×340 mm, height: 25 mm, inner surface: Teflon (registered trademark) coating) in an atmospheric air open system. Shortly after the pouring, a polymerization reaction started. Note that the stainless steel vat-type reaction apparatus was preset to have a surface temperature of 50° C. with use of a hot plate (NEO HOTPLATE HI-1000; available from Iuchi Seieido Co. Ltd.).

As the polymerization reaction proceeded, the polymerization reaction caused expansion and foaming in various directions upward of the vat-type reaction apparatus while water vapor was generated, and, after that, caused shrinkage to a size slightly larger than the bottom surface of the reaction apparatus. A polymerization product obtained by this operation was assumed to be a comparative hydrogel polymer (1). Note that this polymerization reaction (expansion and shrinkage) ended within approximately 1 minute. After that, the comparative hydrogel polymer (1) was retained in the reaction apparatus for 3 minutes. Note that these series of operations were carried out in an atmospheric air open system.

The obtained comparative hydrogel polymer (1) was crushed with use of a meat chopper (No. 32 type, available from Hiraga Seisakusho Co., Ltd.) equipped with a die having a die hole diameter of 9.5 mm. Note that the gel crushing was carried out by charging the comparative hydrogel polymer (1) at 2.4 (kg/min) and water vapor at 5.0 (kg/h) into the meat chopper in a state in which the rotation speed of the screw shaft of the meat chopper was set to 130 rpm.

Next, the comparative hydrogel polymer (1) was dried with use of a hot-air dryer to obtain a comparative dried polymer (1). The drying was carried out by spreading, onto a stainless steel metal gauze having a mesh size of 850 μm, the comparative hydrogel polymer (1) crushed with the meat chopper and allowing hot air of 180° C. to pass through for 30 minutes.

The comparative dried polymer (1) was pulverized with use of a roll mill (WML-type roll pulverizer, available from Inokuchi Giken Ltd.), and was then classified with use of JIS sieves having respective mesh sizes of 850 μm and 150 μm to obtain comparative water-absorbing resin powder (1) having a non-uniformly pulverized shape. The mass average particle diameter of the comparative water-absorbing resin powder (1) was 340 μm.

100 parts by mass of the comparative water-absorbing resin powder (1) and a surface-crosslinking agent solution composed of 0.024 parts by mass of ethylene glycol diglycidyl ether, 0.308 parts by mass of ethylene carbonate, 0.515 parts by mass of propylene glycol, and 2.08 parts by mass of ion-exchanged water were mixed uniformly. A resulting mixture was introduced into a heat treatment machine adjusted to an atmospheric temperature of 190° C.±2° C. and heat-treated for 30 minutes. Then, the powder temperature was forcibly cooled to 60° C. to obtain surface-crosslinked comparative water-absorbing resin powder (1).

To 100 parts by mass of the surface-crosslinked comparative water-absorbing resin powder (1), a solution composed of 0.022 parts by mass of 45 mass % trisodium salt of diethylenetriamine pentaacetate, and 1 part by mass of ion-exchanged water was mixed uniformly to obtain comparative water-absorbing resin particles (1).

To 100 parts by mass of the obtained comparative water-absorbing resin particles (1), 0.35 parts by mass of silicon dioxide (REOLOSIL (registered trademark) QS-20, available from Oriental Silicas Corporation) in the form of fine particles was added and mixed to obtain comparative water-absorbing resin particles (1). Tables 1 to 3 show physical properties of the obtained comparative water-absorbing resin (1).

TABLE 1

Physical properties of water-absorbing resins

| | | CRC [g/g] | AAP [g/g] | Ext [mass %] | Moisture content [mass %] | D50 [μm] | Bulk density [g/cm$^3$] |
|---|---|---|---|---|---|---|---|
| Example 1 | Water-absorbing resin (1) | 31.6 | 20.0 | 19.1 | 11.8 | 390 | 0.70 |
| Example 2 | Water-absorbing resin (2) | 34.2 | 23.7 | 22.1 | 13.5 | 120 | 0.81 |
| Example 3 | Water-absorbing resin (3) | 33.3 | 14.6 | 22.2 | 12.5 | 410 | 0.69 |

TABLE 1-continued

Physical properties of water-absorbing resins

| | | CRC [g/g] | AAP [g/g] | Ext [mass %] | Moisture content [mass %] | D50 [μm] | Bulk density [g/cm³] |
|---|---|---|---|---|---|---|---|
| Comparative Example 1 | Comparative water-absorbing resin (1) | 33.0 | 18.0 | 17.0 | 1.0 | 350 | 0.62 |

TABLE 2

Swollen gel compressibility rates of water-absorbing resins

| | | Thickness of swollen gel before compression D1 [mm] | Thickness of swollen gel after compression D2 [mm] | Swollen gel compressibility rate (D1 − D2)/D1 × 100 [%] |
|---|---|---|---|---|
| Example 1 | Water-absorbing resin (1) | 13.66 | 13.05 | 4.5 |
| Example 2 | Water-absorbing resin (2) | 15.50 | 14.36 | 7.4 |
| Example 3 | Water-absorbing resin (3) | 15.62 | 15.13 | 3.1 |
| Comparative Example 1 | Comparative water-absorbing resin (1) | 11.69 | 11.78 | −0.8 |

TABLE 3

Results of evaluation of absorbent sheets for evaluation

| | | Thickness of absorbent sheet before compression D1' [mm] | Thickness of absorbent sheet after compression D2' [mm] | Thickness compressibility rate (D1' − D2')/D1' × 100 [%] |
|---|---|---|---|---|
| Example 1 | Water-absorbing resin (1) | 15.4 | 6.0 | 61 |
| Example 2 | Water-absorbing resin (2) | 17.1 | 6.0 | 65 |
| Example 3 | Water-absorbing resin (3) | 14.9 | 6.1 | 59 |
| Comparative Example 1 | Comparative water-absorbing resin (1) | 11.7 | 9.1 | 22 |

From Tables 1 to 3, the following can be found. The water-absorbing resins (1) to (3) in Examples 1 to 3 have a swollen gel compressibility rate of 3% or more, and can be described as water-absorbing resins that enable provision of an absorbent article that prevents swelling of a water-absorbing portion when used in a thin absorbent article. On the other hand, the comparative water-absorbing resin (1) in Comparative Example 1 has small absolute values of D1 and D2, which are the thicknesses of the swollen gel, but has a minus swollen gel compressibility rate (%), and the thickness D2 after the application of load is rather larger than the thickness D1 before the application of load. Further, as shown in Table 3, when the comparative water-absorbing resin (1) of Comparative Example 1 is used in an absorbent sheet, the absorbent sheet after the application of load is thicker than those in Examples 1 to 3.

INDUSTRIAL APPLICABILITY

A water-absorbing resin and an absorbent body in accordance with an embodiment of the present invention enable provision of an absorbent article that prevents swelling of a water-absorbing portion when used in a thin absorbent article. Therefore, the water-absorbing resin and the absorbent body in accordance with an embodiment of the present invention can be suitably utilized for the application of an absorbent body in an absorbent article such as disposable diapers (for infants and for adults), sanitary napkins, and incontinence pads.

REFERENCE SIGNS LIST

10: swollen gel compressibility rate measurement device
11: cell
12: piston
13: petri dish
14: weight
15: bottom portion
16: water-absorbing resin
20: absorbent sheet for evaluation
10 21: adhesive tape
22: water-absorbing resin spread area
23: nonwoven fabric

The invention claimed is:

1. A water-absorbing resin, wherein said water-absorbing resin is a particulate poly(meth)acrylic acid (salt)-based water-absorbing resin and has a swollen gel compressibility rate of 3% or more expressed by the following (Formula 1):

$$\text{Swollen gel compressibility rate [\%]} = (D1 - D2)/D1 \times 100, \quad \text{(Formula 1)}$$

where D1 is a thickness [mm] of a swollen gel layer formed by the water-absorbing resin when a measurement device which is equipped with a piston having a diameter of 59 mm and a cell having a bottom portion in a mesh form and having an inner diameter of 60 mm and in which 1.0 g of the water-absorbing resin is spread on the bottom portion has been placed in a petri dish containing a 0.9 mass % aqueous sodium chloride solution to allow the water-absorbing resin to absorb the 0.9 mass % aqueous sodium chloride solution for 5 minutes, and D2 is a thickness [mm] of the swollen gel layer formed by the water-absorbing resin after an operation of setting the measurement device on a sieve having a mesh size of 4750 μm, placing a weight on the piston so that a load of 0.7 psi is applied to the swollen gel layer, allowing the cell to stand still for 10 seconds, and then removing the weight has been repeated ten times.

2. The water-absorbing resin according to claim 1, which is an aggregate-like particle of spherical particles.

3. The water-absorbing resin according to claim 1, which has a mass average particle diameter (D50) of 50 μm to 700 μm.

4. The water-absorbing resin according to claim 1, wherein the thickness D2 is less than 15 mm.

5. The water-absorbing resin according to claim 1, wherein the thickness D1 is less than 15 mm.

6. The water-absorbing resin according to claim 1, which has a water absorption capacity under pressure (AAP) of 18 g/g or more.

7. The water-absorbing resin according to claim 1, which is obtained by carrying out reversed phase suspension polymerization in a hydrophobic organic solvent.

8. The water-absorbing resin according to claim 1, which is obtained by extruding spherical particles using an extruder having a porous plate.

9. An absorbent body, wherein said absorbent body contains a water-absorbing resin according to claim 1, and (1) does not contain hydrophilic fibers or (2) contains hydrophilic fibers and is such that a mass of the water-absorbing resin accounts for 50 mass % or more of 100 mass % in total of the water-absorbing resin and the hydrophilic fibers.

* * * * *